(12) United States Patent
Whitcomb

(10) Patent No.: US 6,472,131 B1
(45) Date of Patent: Oct. 29, 2002

(54) ASYMMETRIC SILVER SALT DIMERS AND IMAGING COMPOSITIONS, MATERIALS AND METHODS USING SAME

(75) Inventor: David R. Whitcomb, Woodbury, MN (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/812,597

(22) Filed: Mar. 20, 2001

Related U.S. Application Data
(60) Provisional application No. 60/201,857, filed on May 4, 2000.

(51) Int. Cl.[7] .............................................. G03L 1/498
(52) U.S. Cl. ....................... 430/350; 430/617; 430/619; 430/620; 503/210
(58) Field of Search ................................ 430/350, 619, 430/617, 620; 503/210

(56) References Cited

U.S. PATENT DOCUMENTS

| | | | |
|---|---|---|---|
| 3,330,663 A | | 7/1967 | Weyde et al. |
| 4,603,103 A | | 7/1986 | Hirai et al. |
| 5,350,669 A | * | 9/1994 | Whitcomb et al. ......... 430/618 |
| 5,491,059 A | | 2/1996 | Whitcomb |
| 5,677,121 A | | 10/1997 | Tsuzuki |
| 6,159,667 A | | 12/2000 | Emmers et al. |
| 6,207,614 B1 | | 3/2001 | Defieuw et al. |

FOREIGN PATENT DOCUMENTS

| | | |
|---|---|---|
| EP | 0 962 814 A1 | 12/1999 |
| EP | 0 962 815 A1 | 12/1999 |
| EP | 0 964 300 A1 | 12/1999 |

OTHER PUBLICATIONS

F. Jaber et al, "Preparation and Crystal Structure of Tetraaqua–Bis(Hydrogenopyridine–2–3–(Dicarboxylate) Bis(Pyridine–2–3–Dicarboxyate) . . . ", *Polyhedron* vol. 15, no. 17 pp 2909–2913, 1996.

D. Edwards et al, "Coordination modes of the cyanoacetate ion; silver (I) and bis(n–cyclopentadienyl) titanium(IV) cyanoacetates . . ." *Polyhedron* vol. 16, No. 1, pp 25–31, 1997.

G. Smith et al, "The Crystal Structure of Silver (I) Glycolate Hemihydrate", *Aust. J. Chem.*, 1994, 47, 1179–1183.

G. Smith et al, Preparation and Crystal Structure of Silver (I) Anthranilate, *Aust. J. Chem.*, 1999, 52, pp 325–327.

M. N. Tahir et al, Poly[bis(p–nitrosalicylate–O:O')disilver(I)–O³:Ag';Ag:O³', *Acta Crystallographica* Section C. 1996, pp 593–600.

Deloume et al, Structure Cristalline du Pyridinecarboxylate–2d' Argent(I), Ag($C_5H_4NCO_2H_{1/2}$)$_2H_2$), *Acta Cryst* (1977) B33, 2709–2712.

Ino et al, "Structural Studies of Silver(I) Coordination Polymers with Aryl Iodide derived Ligands", *Inorg. Chem.* 2000, 39, 2146–2151.

Nomiya et al, "Synthesis and crystal structure of three silver(I) complexes with . . .", *j. of The Royal Society of Chemistry* (2000) pp. 1343–1348.

Faber et al, "A new silver(I) carboxylate chelate type: a six–membered ring in the N–oxide picolinate", *Eur. J. Solid State Inorg. Chem.* (1996) t.33 pp. 429–440.

Archibald et al., Synthesis and Characterization of Functionalized N,N'–Diphenylformamidinate Silver(I) Dimers: Solid–State Stuctures and Solution Proerties:, *Inorg. Chem.* (1999), 38, pp 5571–5578.

\* cited by examiner

*Primary Examiner*—Thorl Chea
(74) *Attorney, Agent, or Firm*—J. Lanny Tucker

(57) ABSTRACT

A non-photosensitive silver dimer compound comprises two different silver salts, provided that when the two different silver salts comprise straight-chain, saturated hydrocarbon groups as the silver coordinating ligands, those ligands differ by at least 6 carbon atoms. Many of these silver dimer compounds can be represented by the following Structure I:

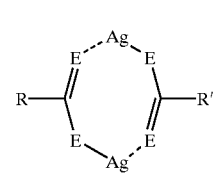

I wherein each E is independently oxygen, sulfur, nitrogen, selenium, or tellurium, R and R' are different alkyl groups, aryl groups, aromatic heterocyclic groups, or halo atoms, provided that when E is oxygen, R and R' are both straight-chain, saturated hydrocarbon groups, those hydrocarbon groups differ from each other by at least 6 carbon atoms. These silver dimer compounds are useful in thermally-developable imaging materials including thermographic and photothermographic materials.

27 Claims, No Drawings

ASYMMETRIC SILVER SALT DIMERS AND IMAGING COMPOSITIONS, MATERIALS AND METHODS USING SAME

This application claims benefit of provisional application No. 60/201,857 filed May 4, 2000.

FIELD OF THE INVENTION

This invention relates to novel non-photosensitive silver dimer compounds and their use in imaging compositions, materials and methods. In particular, it relates to novel silver dimer compounds comprising two different silver salts. These asymmetric dimer compounds are useful in thermally-developable imaging materials such as thermographic and photothermographic imaging materials.

BACKGROUND OF THE INVENTION

Silver-containing thermographic and photothermographic imaging materials (that is, heat-developable photographic materials) that are developed with heat and without liquid development have been known in the art for many years.

Thermography or thermal imaging is a recording process wherein images are generated by the use of thermal energy. In direct thermography, a visible image is formed by image-wise heating a recording material containing matter that changes color or optical density upon heating. Thermographic materials generally comprise a support having coated thereon: (a) a relatively or completely non-photosensitive source of reducible silver ions, (b) a reducing composition (usually including a developer) for the reducible silver ions, and (c) a hydrophilic or hydrophobic binder.

In a typical thermographic construction, the image-forming layers are based on silver salts of long chain fatty acids. Typically, the preferred non-photosensitive reducible silver source is a silver salt of a long chain aliphatic carboxylic acid having from 10 to 30 carbon atoms. The silver salt of behenic acid or mixtures of acids of similar molecular weight are generally used. At elevated temperatures, silver behenate is reduced by a reducing agent for silver ion such as methyl gallate, hydroquinone, substituted-hydroquinones, hindered phenols, catechols, pyrogallol, ascorbic acid, ascorbic acid derivatives, and the like, whereby an image of elemental silver is formed. Some thermographic constructions are imaged by contacting them with the thermal head of a thermographic recording apparatus, such as a thermal printer, thermal facsimile, and the like. In such constructions, an anti-stick layer is coated on top of the imaging layer to prevent sticking of the thermographic construction to the thermal head of the apparatus utilized. The resulting thermographic construction is then heated to an elevated temperature, typically in the range of from about 60 to about 225° C., resulting in the formation of an image.

Thermal recording materials become photothermographic upon incorporating a photosensitive catalyst (such as a silver halide) that upon exposure to irradiation energy (ultraviolet, visible or IR radiation) is capable of providing a latent image. This latent image can be developed by application of thermal energy. Photothermographic materials are also known as "dry silver" materials.

In such materials, the photosensitive catalyst is generally a photographic type photosensitive silver halide that is considered to be in catalytic proximity to the non-photosensitive source of reducible silver ions. Catalytic proximity requires intimate physical association of these two components either prior to or during the thermal image development process so that when silver atoms, (Ag)n, also known as silver specks, clusters, nuclei, or latent image, are generated by irradiation or light exposure of the photosensitive silver halide, those silver atoms are able to catalyze the reduction of the reducible silver ions within a catalytic sphere of influence around the silver atoms [D. Klosterboer, *Imaging Processes and Materials (Neblette's Eighth Edition)*, Sturge, Walworth & Shepp (Eds.), Van Nostrand-Reinhold, New York, Chapter 9, pp. 279–291, 1989]. It has long been understood that silver atoms act as a catalyst for the reduction of silver ions, and that the photosensitive silver halide can be placed in catalytic proximity with the non-photosensitive source of reducible silver ions in a number of different ways (see, for example, *Research Disclosure,* June 1978, item 17029). Other photosensitive materials, such as titanium dioxide, cadmium sulfide, and zinc oxide, have also been reported to be useful in place of silver halide as the photocatalyst in photothermographic materials [see for example, Shepard, *J. Appl. Photog. Eng.* 1982, 8(5), 210–212, Shigeo et al., *Nippon Kagaku Kaishi,* 1994, 11, 992–997, and FR 2,254,047 (Robillard)].

The photosensitive silver halide may be made "in situ," for example, by mixing an organic or inorganic halide-containing source with a source of reducible silver ions to achieve partial metathesis and thus causing the in-situ formation of silver halide (AgX) grains throughout the silver source [see, for example, U.S. Pat. No. 3,457,075 (Morgan et al.)]. In addition, photosensitive silver halides and sources of reducible silver ions can be coprecipitated [see Usanov et al., *J. Imag. Sci. Tech.* 40, 104 (1996)]. Alternatively, a portion of the reducible silver ions can be completely converted to silver halide, and that portion can be added back to the source of reducible silver ions (see Usanov et al., International Conference on Imaging Science, Sep. 7–11, 1998) The silver halide may also be "preformed" and prepared by an "ex situ" process whereby the silver halide (AgX) grains are prepared and grown separately. With this technique, one has the possibility of controlling the grain size, grain size distribution, dopant levels, and composition much more precisely, so that one can impart more specific properties to both the silver halide grains and the photothermographic material. The preformed silver halide grains may be introduced prior to, and be present during, the formation of the source of reducible silver ions. Co-precipitation of the silver halide and the source of reducible silver ions provides a more intimate mixture of the two materials [see for example, U.S. Pat. No. 3,839,049 (Simons)]. Alternatively, the preformed silver halide grains may be added to and physically mixed with the source of reducible silver ions.

The non-photosensitive source of reducible silver ions is a material that contains reducible silver ions. Typically, the preferred non-photosensitive source of reducible silver ions is a silver salt of a long chain aliphatic carboxylic acid having from 10 to 30 carbon atoms, or mixtures of such salts. Such acids are also known as "fatty acids" or "fatty carboxylic acids" . Silver salts of other organic acids or other organic compounds, such as silver imidazoles, silver tetrazoles, silver benzotriazoles, silver benzotetrazoles, silver benzothiazoles and silver acetylides have also been proposed. U.S. Pat. No. 4,260,677 (Winslow et al.) discloses the use of complexes of various inorganic or organic silver salts.

In photothermographic materials, exposure of the photographic silver halide to light produces small clusters containing silver atoms $(Ag^0)_n$. The imagewise distribution of these clusters, known in the art as a latent image, is generally not visible by ordinary means. Thus, the photosensitive material must be further developed to produce a visible image. This is accomplished by the reduction of silver ions that are in catalytic proximity to silver halide grains bearing the silver containing-clusters of the latent image. This produces a black-and-white image. The non-photosensitive silver source is catalytically reduced to form the visible black-and-white negative image while much of the silver halide, generally, remains as silver halide and is not reduced.

In photothermographic materials, the reducing agent for the reducible silver ions, often referred to as a "developer," may be any compound that, in the presence of the latent image, can reduce silver ion to metallic silver and is preferably of relatively low activity until it is heated to a temperature sufficient to cause the reaction. A wide variety of classes of compounds have been disclosed in the literature that function as developers for photothermographic materials. At elevated temperatures, the reducible silver ions are reduced by the reducing agent for silver ion. In photothermographic materials, upon heating, this reaction occurs preferentially in the regions surrounding the latent image. This reaction produces a negative image of metallic silver having a color that ranges from yellow to deep black depending upon the presence of toning agents and other components in the imaging layer(s).

Differences Between Photothermography and Photography

The imaging arts have long recognized that the field of photothermography is clearly distinct from that of photography. Photothermographic materials differ significantly from conventional silver halide photographic materials that require processing with aqueous processing solutions.

As noted above, in photothermographic imaging materials, a visible image is created by heat as a result of the reaction of a developer incorporated within the material. Heating at 50° C. or more is essential for this dry development. In contrast, conventional photographic imaging materials require processing in aqueous processing baths at more moderate temperatures (from 30° C. to 50° C.) to provide a visible image.

In photothermographic materials, only a small amount of silver halide is used to capture light and a non-photosensitive source of reducible silver ions (for example, a silver carboxylate) is used to generate the visible image using thermal development. Thus, the imaged photosensitive silver halide serves as a catalyst for the physical development process involving the non-photosensitive source of reducible silver ions and the incorporated reducing agent. In contrast, conventional wet-processed, black-and-white photographic materials use only one form of silver (that is, silver halide) that, upon chemical development, is itself converted into the silver image, or that upon physical development requires addition of an external silver source (or other reducible metal ions that form black images upon reduction to the corresponding metal). Thus, photothermographic materials require an amount of silver halide per unit area that is only a fraction of that used in conventional wet-processed photographic materials.

In photothermographic materials, all of the "chemistry" for imaging is incorporated within the material itself. For example, they include a developer (that is, a reducing agent for the reducible silver ions) while conventional photographic materials usually do not. Even in so-called "instant photography", the developer chemistry is physically separated from the photosensitive silver halide until development is desired. The incorporation of the developer into photothermographic materials can lead to increased formation of various types of "fog" or other undesirable sensitometric side effects. Therefore, much effort has gone into the preparation and manufacture of photothermographic materials to minimize these problems during the preparation of the photothermographic emulsion as well as during coating, use, storage, and post-processing handling.

Moreover, in photothermographic materials, the unexposed silver halide generally remains intact after development and the material must be stabilized against further imaging and development. In contrast, silver halide is removed from conventional photographic materials after solution development to prevent further imaging (that is, in the aqueous fixing step).

In photothermographic materials, the binder is capable of wide variation and a number of binders (both hydrophilic and hydrophobic) are useful. In contrast, conventional photographic materials are limited almost exclusively to hydrophilic colloidal binders such as gelatin.

Because photothermographic materials require dry thermal processing, they present distinctly different problems and require different materials in manufacture and use, compared to conventional, wet-processed silver halide photographic materials. Additives that have one effect in conventional silver halide photographic materials may behave quite differently when incorporated in photothermographic materials where the underlying chemistry is significantly more complex. The incorporation of such additives as, for example, stabilizers, antifoggants, speed enhancers, supersensitizers, and spectral and chemical sensitizers in conventional photographic materials is not predictive of whether such additives will prove beneficial or detrimental in photothermographic materials. For example, it is not uncommon for a photographic antifoggant useful in conventional photographic materials to cause various types of fog when incorporated into photothermographic materials, or for supersensitizers that are effective in photographic materials to be inactive in photothermographic materials.

These and other distinctions between photothermographic and photographic materials are described in *Imaging Processes and Materials* (*Neblette's Eighth Edition*), noted above, *Unconventional Imaging Processes,* E. Brinckman et al. (Eds.), The Focal Press, London and New York, 1978, pp. 74–75, and in Zou et al., *J. Imaging Sci. Technol.* 1996,40, 94–103.

Problem to be Solved

While a number of useful thermographic and photothermographic products are available in the market for medical and graphic arts uses, there is a continuing need for improving the reactivity of the compounds used to provide reducible silver ions. In particular, there is a need for imaging materials that have improved image stability and that can be imaged and/or developed at lower temperatures, while providing high $D_{max}$, and maintaining good image tone and quality.

SUMMARY OF THE INVENTION

The present invention provides a non-photosensitive silver dimer compound comprising two different silver salts, provided that when the two different silver salts comprise straight-chain, saturated hydrocarbon groups as the silver coordinating ligands, those ligands differ by at least 6 carbon atoms.

In preferred embodiments, the non-photosensitive silver dimer compounds of this invention are represented by the following Structure I:

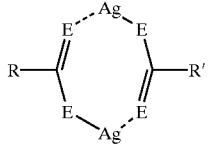

wherein
each E is independently oxygen, sulfur, nitrogen, selenium, or tellurium, R and R' are different alkyl, aryl, aromatic heterocyclic, or halo groups, provided that when E is oxygen, and R and R' are both straight chain saturated hydrocarbon groups, then R and R' differ from each other by at least 6 carbon atoms.

This invention also provides a composition comprising at least first and second non-photosensitive silver dimer compounds, at least the first silver dimer compound being one of those described above for this invention.

This invention further provides a thermally-developable emulsion comprising:
a) a source of non-photosensitive silver that is a silver dimer compound as described above,
b) a reducing composition for the non-photosensitive silver dimer compound, and
c) a binder.

Further, a thermally-developable imaging material comprises a support having thereon, in the same or different thermally-developable imaging layers,
a) a source of non-photosensitive silver that is a silver dimer compound as described above,
b) a reducing composition for the non-photosensitive silver dimer compound, and
c) a binder.

A photothermographic material of this invention comprises a support having thereon, in one or more photothermographic imaging layers:
a) a photosensitive silver halide,
b) a source of non-photosensitive silver that is a silver dimer compound as described above,
c) a reducing composition for the non-photosensitive silver dimer compound, and
d) a binder.

Still again, the present invention includes a method of providing an image comprising imagewise heating the thermally-developable material of this invention.

In addition, a method of providing an image also comprises:
A) imagewise exposing the photothermographic material of this invention to imaging radiation to provide a latent image, and
B) simultaneously or sequentially, heating the exposed photothermographic material to develop the latent image into a visible image.

This invention also comprises a method of making the non-photosensitive silver dimer compounds of this invention, which method comprises one of the following:
A) adding a solution containing silver ions to a dispersion or a solution of a mixture of alkali metal or ammonium salts of organic ligands, or
B) adding a solution containing silver ions to a dispersion of a mixture of alkali metal or ammonium salts of fatty acids at a temperature below the Krafft temperature of the metal or ammonium salts, or
C) adding a solution of silver ion to a solution of a mixture of alkali metal or ammonium salts of fatty acids at a temperature above the Krafft temperature of the metal or ammonium salts.

The solution or dispersion may be in an aqueous or an organic solvent.

Another embodiment of this invention is a method of making a photosensitive imaging composition comprising:
A) preparing a dispersion of photosensitive silver halide grains,
B) adding to the dispersion of photosensitive silver halide grains, silver ions and first and second compounds capable of forming first and second silver salts, respectively, provided that when the first and second compounds capable of forming silver salts comprise straight-chain, saturated hydrocarbon groups as silver coordinating ligands, those ligands differ by at least 6 carbon atoms.

Thermographic and photothermographic materials incorporating the novel silver dimer compounds of this invention as the non-photosensitive silver salts can provide images with improved image stability that can be developed at lower temperatures, while providing high quality images with high $D_{max}$ and good image tone.

DETAILED DESCRIPTION OF THE INVENTION

The thermographic and photothermographic materials of this invention can be used, for example, in conventional black-and-white or color thermography and photothermography, in electronically generated black-and-white or color hardcopy recording, in the graphic arts area (for example, image-setting and phototypesetting), in the manufacture of printing plates, in proofing, in microfilm applications, and in radiographic imaging. Furthermore, the absorbance of these photothermographic materials between 350 and 450 nm is sufficiently low (less than 0.5) to permit their use in graphic arts applications such as contact printing, proofing, and duplicating ("duping"). The present invention is preferably used to obtain black-and-white images.

In the thermographic and photothermographic materials of this invention, the components of the imaging layer can be in one or more layers. The layer(s) that contain a photosensitive photocatalyst (for photothermographic materials) and non-photosensitive source of reducible silver ions, or both, are referred to herein as emulsion layer(s). The photosensitive photocatalyst and the non-photosensitive source of reducible silver ions are in catalytic proximity and preferably in the same emulsion layer.

Various layers are usually disposed on the "backside" (non-emulsion side) of the materials, including antihalation layer(s), protective layers, antistatic layers, conducting layers, and transport enabling layers.

Various layers are also usually disposed on the "frontside" or emulsion side of the support, including protective topcoat layers, primer layers, interlayers, opacifying layers, antistatic layers, antihalation layers, acutance layers, auxiliary layers, and others readily apparent to one skilled in the art.

For the inventive thermographic materials, an image (either a color or black-and-white image) is provided by exposing the materials to heat from a suitable source in an imagewise fashion. Thermal development of the image occurs at essentially the same time.

The present invention also provides a process for the formation of a visible image (usually a black-and-white image) by first exposing to electro-magnetic radiation and thereafter heating the inventive photothermographic material. In one embodiment, the present invention provides a process comprising:

A) imagewise exposing the photothermographic material of this invention to electromagnetic radiation to which the photocatalyst (for example, a photosensitive silver halide) of the material is sensitive, to generate a latent image, and B) simultaneously or sequentially, heating the exposed material to develop the latent image into a visible image.

In some methods of practicing this invention, the imaging method includes the further steps of:

C) positioning the exposed material with a visible image thereon between a source of imaging radiation and an imageable material that is sensitive to the imaging radiation, and D) thereafter exposing the imageable material to the imaging radiation through the visible image in the exposed and developed photothermographic material to provide a visible image in the imageable material.

This visible image can also be used as a mask for exposure of other photosensitive imageable materials, such as graphic arts films, proofing films, printing plates and circuit board films, that are sensitive to suitable imaging radiation (for example UV radiation). This can be done by imaging an imageable material (such as a photopolymer, a diazo material, a photoresist, or a photosensitive printing plate) through the exposed and heat-developed photothermographic material of this invention using steps C) and D) noted above.

When the photothermographic materials of this invention are heat-developed as described below in a substantially water-free condition after, or simultaneously with, imagewise exposure, a silver image (preferably a black-and-white silver image) is obtained. The photothermographic material may be exposed in step A using ultraviolet, visible, infrared or laser radiation using an infrared laser, a laser diode, an infrared laser diode, a light-emitting screen, a CRT tube, a light-emitting diode, or other light or radiation source readily apparent to one skilled in the art.

Definitions

As used herein:

In the descriptions of the thermographic and photothermographic materials of the present invention, "a" or "an" component refers to "at least one" of that component. For example, the silver dimer compounds of this invention can be used individually or in mixtures.

Heating in a substantially water-free condition as used herein, means heating at a temperature of from about 50° to about 250° C. with little more than ambient water vapor present. The term "substantially water-free condition" means that the reaction system is approximately in equilibrium with water in the air and water for inducing or promoting the reaction is not particularly or positively supplied from the exterior to the material. Such a condition is described in T. H. James, *The Theory of the Photographic Process,* Fourth Edition, Macmillan 1977, p. 374.

"Photothermographic material(s)" means a construction comprising at least one photothermographic emulsion layer or a photothermographic set of layers (wherein the silver halide and the source of reducible silver ions are in one layer and the other essential components or desirable additives are distributed, as desired, in an adjacent coating layer) and any supports, topcoat layers, image-receiving layers, blocking layers, antihalation layers, subbing or priming layers. These materials also include multilayer constructions in which one or more imaging components are in different layers, but are in "reactive association" so that they readily come into contact with each other during imaging and/or development. For example, one layer can include the non-photosensitive source of reducible silver ions and another layer can include the reducing composition, but the two reactive components are in reactive association with each other.

"Thermographic material(s)" are similarly defined except that no photosensitive photocatalyst is intentionally present in the imaging layers.

"Emulsion layer", "imaging layer", or "photothermographic emulsion layer" means a layer of a photothermographic material that contains the photosensitive silver halide and/or non-photosensitive source of reducible silver ions. Similarly, "thermographic emulsion layer," means a layer of a thermographic material that contains the non-photosensitive source of reducible silver ions. It can also mean a layer of the thermographic or photothermographic material that contains, in addition to the photosensitive silver halide (when present) and/or non-photosensitive source of reducible ions, additional essential components and/or desirable additives. These layers are usually on what is known as the "frontside" of the support.

"Ultraviolet region of the spectrum" refers to that region of the spectrum less than or equal to 410 nm, and preferably from about 100 nm to about 410 nm, although parts of these ranges may be visible to the naked human eye. More preferably, the ultraviolet region of the spectrum is the region of from about 190 to about 405 nm.

"Visible region of the spectrum" refers to that region of the spectrum of from about 400 nm to about 750 nm.

"Short wavelength visible region of the spectrum" refers to that region of the spectrum of from about 400 nm to about 450 nm.

"Red region of the spectrum" refers to that region of the spectrum of from about 600 nm to about 750 nm.

"Infrared region of the spectrum" refers to that region of the spectrum of from about 750 nm to about 1400 nm.

"Non-photosensitive" means not intentionally light sensitive.

The sensitometric terms "photospeed" or "photographic speed", $D_{min}$, and $D_{max}$ have conventional definitions known in the imaging arts.

"Transparent" means capable of transmitting visible light or imaging radiation without appreciable scattering or absorption.

The Krafft temperature is the temperature above which compounds that are capable of forming micelles, form a sufficient number so as to rapidly increase in solubility. Salts of long chain carboxylic acids have such a property.

As is well understood in this art, for the various compounds described herein (including the silver dimer compounds and silver coordinating ligands), substitution is not only tolerated, but is often advisable and various substituents are anticipated on the compounds used in the present invention. Thus, when a compound is referred to as "having the structure" of a given formula, any substitution that does not alter the bond structure of the formula or the shown atoms within that structure is included within the formula, unless such substitution is specifically excluded by language (such as "free of carboxy-substituted alkyl"). For example, where a benzene ring structure is shown (including fused ring structures), substituent groups may be placed on the benzene ring structure, but the atoms making up the benzene ring structure may not be replaced.

As a means of simplifying the discussion and recitation of certain substituent groups, the term "group" refers to chemical species that may be substituted as well as those that are not so substituted. Thus, when the term "group," is used to describe a substituent, that substituent includes the use of additional substituents beyond the literal definition of the basic group. Where the term "moiety" is used to describe a substituent, only the unsubstituted group is intended to be included. For example, the phrase, "alkyl group" is intended to include not only pure hydrocarbon alkyl chains, such as methyl, ethyl, propyl, t-butyl, cyclohexyl, iso-octyl, and octadecyl, but also alkyl chains bearing substituents known in the art, such as hydroxyl, alkoxy, phenyl, halogen atoms (fluoro, chloro, bromo, and iodo), cyano, nitro, amino, and carboxy. For example, alkyl group includes ether groups (for example $CH_3—CH_2—CH_2—O—CH_2—$ and $CH_3—CH_2—CH_2—S—CH_2—$), haloalkyls, nitroalkyls, carboxyalkyls, hydroxyalkyls, and sulfoalkyls. On the other hand, the phrase "alkyl moiety" or "straight chain alkyl moiety" is limited to the inclusion of only pure hydrocarbon alkyl chains, such as methyl, ethyl, propyl, t-butyl, cyclohexyl, iso-octyl, and octadecyl. Substituents that react with active ingredients, such as very strongly electrophilic or oxidizing substituents, would of course be excluded by the ordinarily skilled artisan as not being inert or harmless.

As used herein, the phrase "silver dimer compounds" that comprise "different silver salts" refers to a molecule comprising two silver atoms and two different silver coordinating ligands. Although each of the units making up these silver dimer compounds are technically silver coordination compounds they are usually also referred to as silver salts.

*Research Disclosure* is a publication of Kenneth Mason Publications Ltd., Dudley House, 12 North Street, Emsworth, Hampshire PO10 7DQ England (also available from Emsworth Design Inc., 147 West 24th Street, New York, N.Y. 10011).

Other aspects, advantages, and benefits of the present invention are apparent from the detailed description, examples, and claims provided in this application.

The Photosensitive Silver Halide

As noted above, the photothermographic materials of the present invention include one or more photocatalysts in the photothermographic emulsion layer(s). Useful photocatalysts are typically silver halides such as silver bromide, silver iodide, silver chloride, silver bromoiodide, silver chlorobromoiodide, silver chlorobromide, and others readily apparent to one skilled in the art. Mixtures of silver halides can also be used in any suitable proportion. Silver bromide and silver bromoiodide are more preferred, with the latter silver halide having up to 10 mol % silver iodide.

The shape of the photosensitive silver halide grains used in the present invention is in no way limited. The silver halide grains may have any crystalline habit including, but not limited to, cubic, octahedral, rhombic dodecahedral, orthorhombic, tetrahedral, other polyhedral, laminar, twinned, platelet, or tabular morphologies and may have epitaxial growth of crystals thereon. If desired, a mixture of these crystals can be employed. Silver halide grains having cubic and tabular morphology are preferred.

The silver halide grains may have a uniform ratio of halide throughout. They may have a graded halide content, with a continuously varying ratio of, for example, silver bromide and silver iodide or they may be of the core-shell type, having a discrete core of one halide ratio, and a discrete shell of another halide ratio. Core-shell silver halide grains useful in photothermographic materials and methods of preparing these materials are described for example in U.S. Pat. No. 5,382,504 (Shor et al.) incorporated herein by reference. Iridium and/or copper doped core-shell and non-core-shell grains are described in U.S. Pat. No. 5,434,043 (Zou et al.) and U.S. Pat. No. 5,939,249 (Zou), incorporated herein by reference.

The photosensitive silver halide can be added to (or formed within) the emulsion layer(s) in any fashion as long as it is placed in catalytic proximity to the non-photosensitive source of reducible silver ions.

It is preferred that the silver halides be preformed and prepared by an ex-situ process. The silver halide grains prepared ex-situ may then be added to and physically mixed with the non-photosensitive source of reducible silver ions. It is more preferable to form the source of reducible silver ions in the presence of ex-situ-prepared silver halide. In this process, the source of reducible silver ions, such as a long chain fatty acid silver carboxylate (commonly referred to as a silver "soap"), is formed in the presence of the preformed silver halide grains. Co-precipitation of the reducible source of silver ions in the presence of silver halide provides a more intimate mixture of the two materials [see, for example U.S. Pat. No. 3,839,049 (Simons)]. Materials of this type are often referred to as "preformed soaps."

The silver halide grains used in the imaging formulations can vary in average diameter of up to several micrometers ($\mu$m) depending on their desired use. Preferred silver halide grains are those having an average particle size of from about 0.01 to about 1.5 $\mu$m, more preferred are those having an average particle size of from about 0.03 to about 1.0 $\mu$m, and most preferred are those having an average particle size of from about 0.05 to about 0.8 $\mu$m. Those of ordinary skill in the art understand that there is a finite lower practical limit for silver halide grains that is partially dependent upon the wavelengths to which the grains are spectrally sensitized. Such a lower limit, for example, is typically from about 0.01 to about 0.005 $\mu$m.

The average size of the photosensitive silver halide grains is expressed by the average diameter if the grains are spherical, and by the average of the diameters of equivalent circles for the projected images if the grains are cubic or in other non-spherical shapes.

Grain size may be determined by any of the methods commonly employed in the art for particle size measurement. Representative methods are described by in "Particle Size Analysis," ASTM Symposium on Light Microscopy, R. P. Loveland, 1955, pp. 94—122, and in C. E. K. Mees and T. H. James, *The Theory of the Photographic Process,* Third Edition, Chapter 2, Macmillan Company, 1966. Particle size measurements may be expressed in terms of the projected areas of grains or approximations of their diameters. These will provide reasonably accurate results if the grains of interest are substantially uniform in shape.

Preformed silver halide emulsions used in the material of this invention can be prepared by aqueous or organic processes and can be unwashed or washed to remove soluble salts. In the latter case, the soluble salts can be removed by ultrafiltration, by chill setting and leaching, or by washing the coagulum [for example, by the procedures described in U.S. Pat. No. 2,618,556 (Hewitson et al.), U.S. Pat. No. 2,614,928 (Yutzy et al.), U.S. Pat. No. 2,565,418 (Yackel), U.S. Pat. No. 3,241,969 (Hart et al.), and U.S. Pat. No. 2,489,341 (Waller et al.)].

It is also effective to use an in situ process in which a halide-containing compound is added to an organic silver salt to partially convert the silver of the organic silver salt to silver halide. The halogen-containing compound can be inorganic (such as zinc bromide or lithium bromide) or organic (such as N-bromosuccinimide).

Additional methods of preparing these silver halide and organic silver salts and manners of blending them are described in *Research Disclosure,* June 1978, item 17029, U.S. Pat. No. 3,700,458 (Lindholm) and U.S. Pat. No. 4,076,539 (Ikenoue et al.), and JP Applications 13224/74, 42529/76, and 17216/75.

The one or more photosensitive silver halides used in the photo-thermographic materials of the present invention are preferably present in an amount of from about 0.005 to about 0.5 mole, more preferably from about 0.01 to about 0.25 mole per mole, and most preferably from about 0.03 to about 0.15 mole, per mole of non-photosensitive source of reducible silver ions.

Cheincal and Spectral Sensitizers

The photosensitive silver halides used in the invention may be may be employed without modification. However, they are preferably chemically and/or spectrally sensitized in a manner similar to that used to sensitize conventional wet-processed silver halide photographic materials or state-of-the-art heat-developable photothermographic materials.

Thus, the photosensitive silver halides may be chemically sensitized with one or more chemical sensitizing agents, such as a compound containing sulfur, selenium, tellurium, gold, platinum, palladium, ruthenium, rhodium, iridium, or combinations thereof, a reducing agent such as a tin halide or a combination of any of these. The details of these procedures are described in T. H. James, *The Theory of the Photographic Process,* Fourth Edition, Chapter 5, pp. 149–169. Suitable chemical sensitization procedures are also disclosed in U.S. Pat. No. 1,623,499 (Sheppard et al.), U.S. Pat. No. 2,399,083 (Waller et al.), U.S. Pat. No. 3,297,447 (McVeigh), U.S. Pat. No. 3,297,446 (Dunn), U.S. Pat. No. 5,049,485 (Deaton), U.S. Pat. No. 5,252,455 (Deaton), U.S. Pat. No. 5,391,727 (Deaton), U.S. Pat. No. 5,912,111 (Lok et al.), U.S. Pat. No. 5,759,761 (Lushington et al.), and EP-A-0 915 371 (Lok et al.).

One method of chemical sensitization is by oxidative decomposition of a spectral sensitizing dye in the presence of a photothermographic emulsion, as described in U.S. Pat. No. 5,891,615 (Winslow et al.) incorporated herein by reference.

Sulfur-containing chemical sensitizers useful in the present invention are well known in the art and described for example, in Sheppard et al., J. Franklin Inst., 1923, 196, pp. 653 and 673, C. E. K. Mees and T. H. James, *The Theory of the Photographic Process,* $4^{th}$ Edition, 1977, pp. 152–3, Tani, T., *Photographic Sensitivity: Theory and Mechanisms,* Oxford University Press, NY, 1995, pp. 167–176, U.S. Pat. No. 5,891,615 (Winslow et al.), Zavlin et al., IS&T's $48^{th}$ Annual Conference Papers, May 7–11 1995 Washington D.C., pp. 156–6), U.S. Pat. No. 4,810,626 (Burgmaier et al.), U.S. Pat. No. 4,036,650 (Kobayashi et al.), U.S. Pat. No. 4,213,784 (Ikenoue et al.), and U.S. Pat. No. 4,207,108 (Hiller).

Particularly useful sulfur-containing chemical sensitizers are substituted thiourea ligands that include any —S=C(—N<)—N< group that has one or more of the two remaining valences on each nitrogen atom substituted with hydrogen or with the same or different aliphatic substituents. More preferably, the four nitrogen valences are substituted with the same aliphatic substituent. Such useful thioureas are described for example in U.S. Pat. No. 5,843,632 (Eshelman et al.) and in copending and commonly assigned U.S. Ser. No. 09/667,748 (filed Sep. 21, 2000 by Lynch, Simpson, Shor, Willett, and Zou, incorporated herein by reference.

Particularly, useful tellurium-containing chemical sensitizing compounds are described in copending and commonly assigned U.S. Ser. No. 09/746,400, filed Dec. 21, 2000 by Lynch, Opatz, Shor, Simpson, Willett, and Gysling, incorporated herein by reference.

Useful combinations of sulfur- or tellurium-containing chemical sensitizers with gold(III) chemical sensitizers are described in copending and commonly assigned U.S. Ser. No. 09/768,094, filed Jan. 24, 2001 by Simpson, Whitcomb, and Shor, incorporated herein by reference.

The total amount of chemical sensitizers that may be used during formulation of the imaging composition will generally vary depending upon the average size of silver halide grains. The total amount is generally at least $10^{-10}$ mole per mole of total silver, and preferably from $10^{-8}$ to about $10^{-2}$ mole per mole of total silver for silver halide grains having an average size of from about 0.01 to about 2 $\mu$m. The upper limit can vary depending upon the compound used, the level of silver halide and the average grain size, and it would be readily determinable by one of ordinary would be readily determinable by one of ordinary skill in the art.

In general, it may also be desirable to add spectral sensitizing dyes to enhance silver halide sensitivity to ultraviolet, visible and infrared light. Thus, the photosensitive silver halides may be spectrally sensitized with various dyes that are known to spectrally sensitize silver halide. Non-limiting examples of sensitizing dyes that can be employed include cyanine dyes, merocyanine dyes, complex cyanine dyes, complex merocyanine dyes, holopolar cyanine dyes, hemicyanine dyes, styryl dyes, and hemioxanol dyes. The cyanine dyes, merocyanine dyes and complex merocyanine dyes are particularly useful. Suitable sensitizing dyes such as those described in U.S. Pat. No. 3,719,495 (Lea), U.S. Pat. No. 5,393,654 (Burrows et al.), U.S. Pat. No. 5,441,866 (Miller et al.), U.S. Pat. No. 5,541,054 (Miller et al.), U.S. Pat. No. 5,281,515 (Delprato et al.), and U.S. Pat. No. 5,314,795 (Helland et al.) are effective in the practice of the invention.

An appropriate amount of spectral sensitizing dye added is generally about $10^{-10}$ to $10^{-1}$ mole, and preferably, about $10^{-7}$ to $10^{-2}$ mole per mole of silver halide.

To further control the properties of photothermographic materials, (for example, contrast, $D_{min}$, speed, or fog), it may be preferable to add one or more heteroaromatic mercapto compounds or heteroaromatic disulfide compounds as "supersensitizers". Examples include compounds of the formulae: Ar—S—M and Ar—S—S—Ar, wherein M represents a hydrogen atom or an alkali metal atom and Ar represents a heteroaromatic ring or fused heteroaromatic ring containing one or more of nitrogen, sulfur, oxygen, selenium, or tellurium atoms. Preferably, the heteroaromatic ring comprises benzimidazole, naphthimidazole, benzothiazole, naphthothiazole, benzoxazole, naphthoxazole, benzoselenazole, benzotellurazole, imidazole, oxazole, pyrazole, triazole, thiazole, thiadiazole, tetrazole, triazine, pyrimidine, pyridazine, pyrazine, pyridine, purine, quinoline, or quinazolinone. Compounds having other heteroaromatic rings and compounds providing enhanced sensitization at other wavelengths are also envisioned to be suitable. Many of the above compounds are described in EP-A-0 559 228 (Philip Jr. et al.) as supersensitizers for infrared photothermographic materials.

The heteroaromatic ring may also carry substituents. Examples of preferred substituents are halo groups (such as bromo and chloro), hydroxy, amino, carboxy, alkyl groups (for example, of 1 or more carbon atoms and preferably 1 to 4 carbon atoms), and alkoxy groups (for example, of 1 or more carbon atoms and preferably of 1 to 4 carbon atoms).

Heteroaromatic mercapto compounds are most preferred. Examples of preferred heteroaromatic mercapto compounds are 2-mercaptobenzimidazole, 2-mercapto-5-methylbenzimidazole, 2-mercaptobenzothiazole and 2-mercaptobenzoxazole, and mixtures thereof.

If used, a heteroaromatic mercapto compound is generally present in an emulsion layer in an amount of at least about 0.0001 mole per mole of total silver in the emulsion layer. More preferably, the heteroaromatic mercapto compound is present within a range of about 0.001 mole to about 1.0 mole, and most preferably, about 0.005 mole to about 0.2 mole, per mole of total silver.

Non-Photosensitive Reducible Silver Source Material

The primary source of non-photosensitive reducible silver ions in the practice of this invention are the silver dimer compounds described herein that comprise two different silver salts (described in detail below). Besides the limitations described below, there are no particular limitations on the structure of the silver salts.

When the two different silver salts comprise straight-chain, saturated hydrocarbon groups as silver coordinating ligands, those ligands differ by at least 6 carbon atoms, and preferably they differ by at least 8 carbon atoms.

In preferred embodiments, the silver dimer compounds of this invention are represented by the following Structure I:

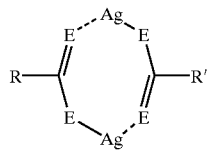

wherein
each E is independently oxygen, sulfur, nitrogen, selenium, or tellurium, R and R' are different groups selected from alkyl groups, aryl groups, aromatic heterocyclic groups, and halo groups, provided that when E is oxygen, and R and R' are both straight-chain, saturated hydrocarbon groups, then R and R' differ by at least 6 carbon atoms (preferably at least 8 carbon atoms, and more preferably at least 12 carbon atoms).

For the compounds of Structure I, E is preferably oxygen, sulfur, or nitrogen, and more preferably, it is oxygen.

R and R' are different substituted or unsubstituted alkyl groups having from 4 to 30 carbon atoms (preferably from 12 to 22 carbon atoms), substituted or unsubstituted aryl groups having from 6 to 14 carbon atoms in the aromatic ring system, substituted or unsubstituted aromatic heterocyclic groups having from 4 to 10 carbon and heteroatoms in the ring system, or halo groups or atoms (such as fluoro, chloro, bromo, and iodo groups). R and R' can be selected from the same or different type of group. For example, R can be an alkyl group while R' is an aryl group, R and can be a halo group while R' is an aromatic heterocyclic group, or R and R' can be different alkyl group or different aryl groups.

Examples of useful alkyl groups for R and R' include, but are not limited to, undecyl, tridecyl, pentadecyl, heptadecyl, nonadecyl, and heneisosyl.

Examples of useful aryl groups for R and R' include, but are not limited to, phenylcarboxylic acid, tetrachlorophenylcarboxylic acid, methylbenzoate, phenyl, p-(4-chlorobenzoyl)phenyl, 4-dodecyloxyphenyl, dihydroxyphenyl, and naphtyl.

Examples of useful aromatic heterocyclic groups for R and R' include, but are not limited to, picolinyl, furoyl, and thiopheneyl.

Each or both of R and R' can also comprise thioalkylene or oxyalkylene groups (that is, alkyl groups interrupted in the chain with one or more thio or oxy groups, or both), for example as described in U.S. Pat. No. 5,491,059 (Whitcomb), incorporated herein by reference.

In preferred embodiments, R and R' are different alkyl groups each having at least 12 carbon atoms, such as R being an alkyl group of 12 to 24 carbon atoms, and R' being an alkyl group of 14 to 24 carbon atoms.

In other preferred embodiments, at least one of R and R' is an aryl group such as phenyl, phenylcarboxylic acid, and tetrachlorophenylcarboxylic acid.

Representative non-photosensitive silver dimer compounds useful in the present invention are shown below. These representations are exemplary and are not intended to be limiting.

TABLE I

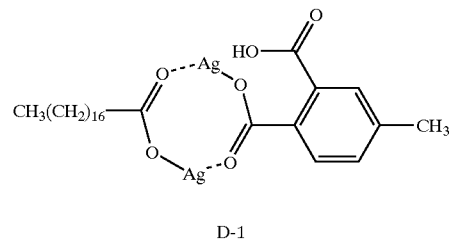

D-1

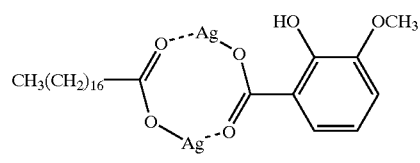

D-2

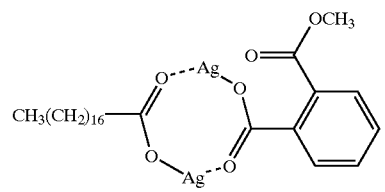

D-3

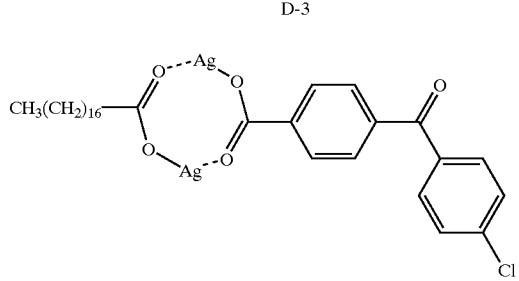

D-4

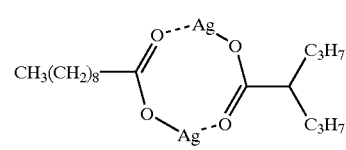

D-5

TABLE I-continued
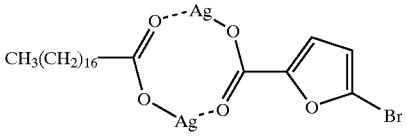
D-6
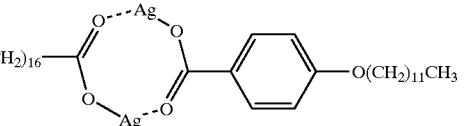
D-7
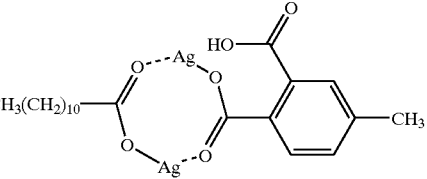
D-8
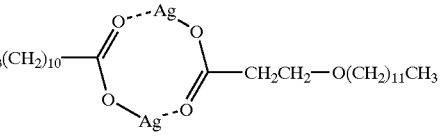
D-9
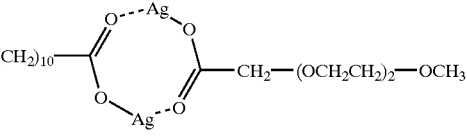
D-10
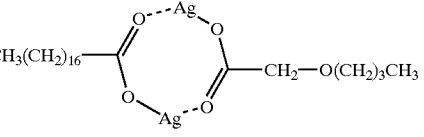
D-11
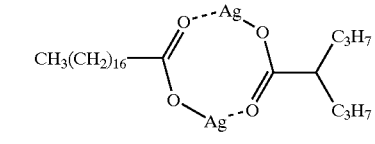
D-12
TABLE I-continued
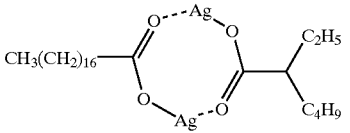
D-13
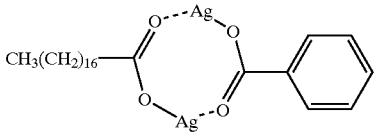
D-14
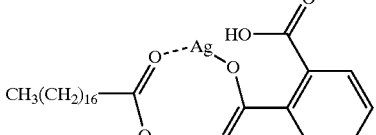
D-15
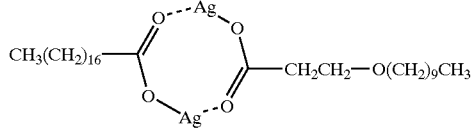
D-16
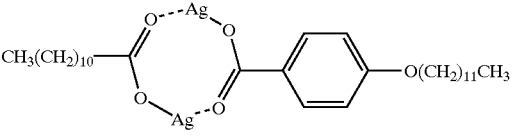
D-17
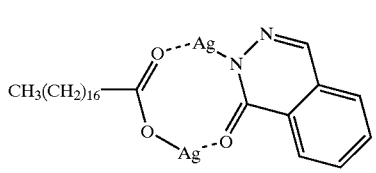
D-18

TABLE I-continued
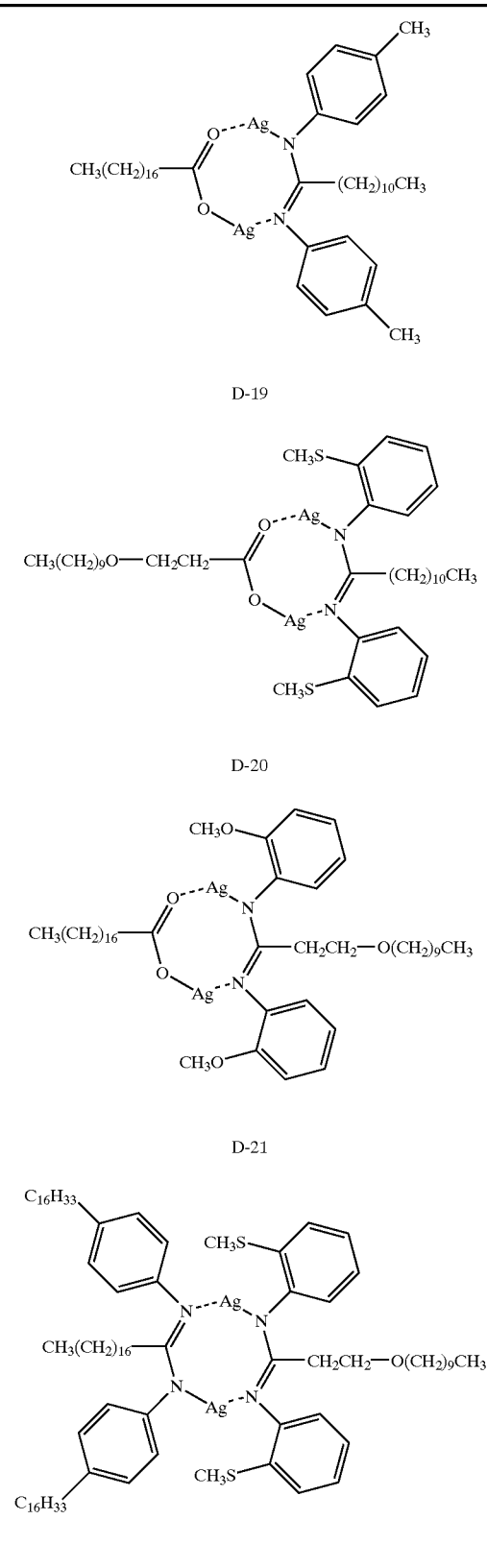
D-19
D-20
D-21
D-22
TABLE I-continued
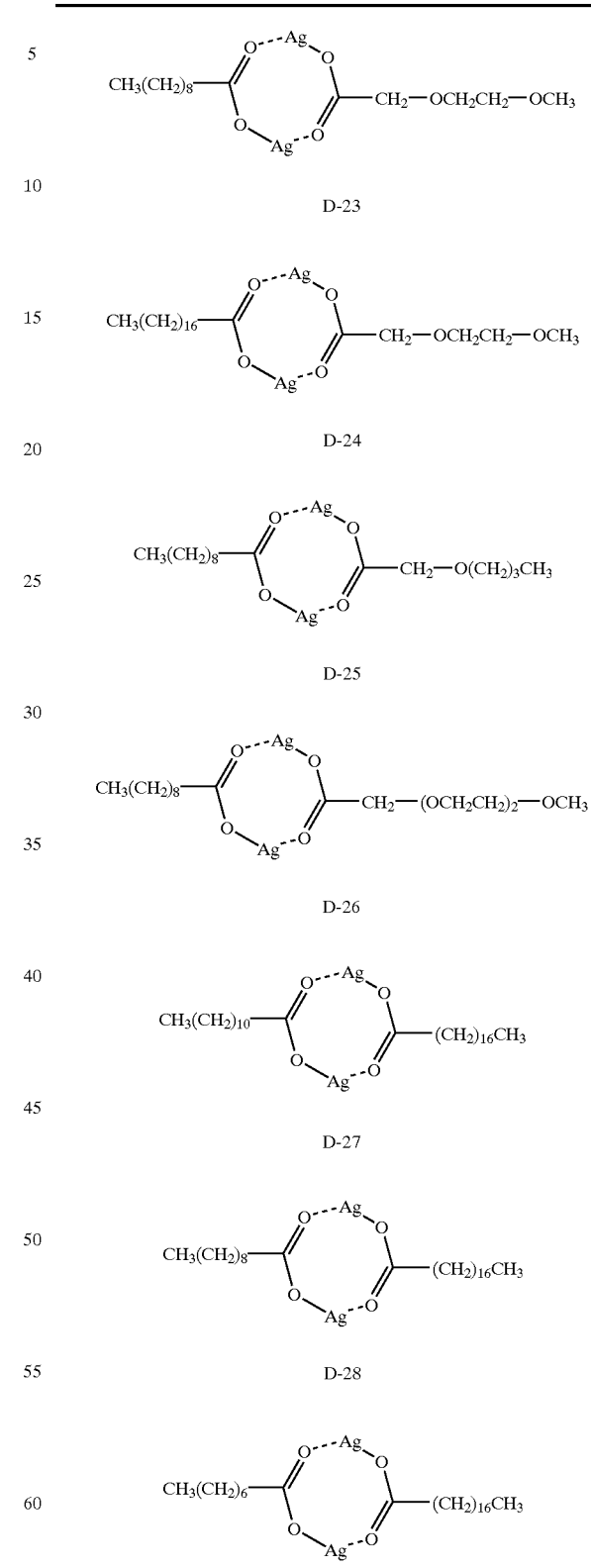
D-23
D-24
D-25
D-26
D-27
D-28
D-29

TABLE I-continued

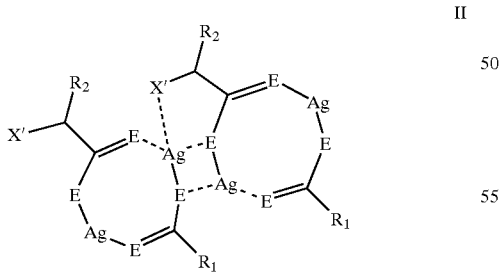

D-30

In some embodiments, a composition (or mixture) of two or more of the described silver dimer compounds are used in the practice of the invention. Each of the silver dimer compounds in such a composition comprises two different silver salts, and at least one silver salt of the first silver dimer compound is different from at least one silver salt of a second silver dimer compound. Moreover, when the two different silver salts in one or more of the dimer compounds comprise straight-chain, saturated hydrocarbon groups as silver coordinating ligands, those ligands differ by at least 6 carbon atoms.

In addition, the silver dimer compounds of this invention can be composed as "core-shell" compounds comprising one or more silver dimer compounds in the "core", and one or more different silver dimer compounds in the "shell", but at least one of the silver dimer compound in the core being different from at least one silver dimer compound in the shell. The preparation of such core-shell compositions would be readily apparent from the teaching provided herein as well as that provided in copending and commonly assigned U.S. Ser. No. 09/761,954 filed Jan. 17, 2001 by Whitcomb and Pham on Provisional Application No. 60/201,858, filed May 4, 2000 by Whitcomb.

In still other embodiments of this invention, one or more of the silver salts in the silver dimer compounds comprise a carboxylate that either has at least 2 carbon atoms and is substituted in the α-position, or has at least 3 carbon atoms and is substituted in the β-position, the carboxylate compound being substituted in the α- or β-position with a ligand that is capable of forming a coordinate covalent bond with silver ions. In preferred embodiments of this type, the α- or β-substituted carboxylate has at least 8 carbon atoms (and more preferably at least 12 carbon atoms).

Such α-and β-substituted carboxylate compounds can be represented, for example, by the following Structure II:

II wherein
E is oxygen, and X' is a silver covalent bond coordinating moiety $R_1$ is R or R' as defined above or differs by having a different X' moiety, and $R_2$ is hydrogen, an alkyl group, an aryl group, an aromatic heterocyclic group, or a silver covalent bond coordinating moiety as defined for X'. Alkyl and aromatic heterocyclic groups are defined as for R and R'.

X' can be a ligand, group or moiety capable of forming a covalent or coordinate bond with silver, for example, a Group VA atom, a Group VIA atom, a Group VIIA atom, a cyano group, and an imino (—C=N—) group, such as fluorine, chlorine, bromine, oxygen, nitrogen, sulfur, and selenium, a cyano group, an imino group, or an olefin. More particularly, useful ligands comprise a silver covalent bond coordinating moiety selected from the group consisting of a Group VIIA atom, nitrogen, sulfur, selenium, or oxygen atoms, and their heteroaromatic or alkyl derivatives.

Thus, the silver dimer compounds of this invention can comprise two different carboxylates, at least one of which is substituted in its α- or β-position with the silver coordinate covalent bond forming ligand.

Representative non-photosensitive silver dimer compounds are shown below.

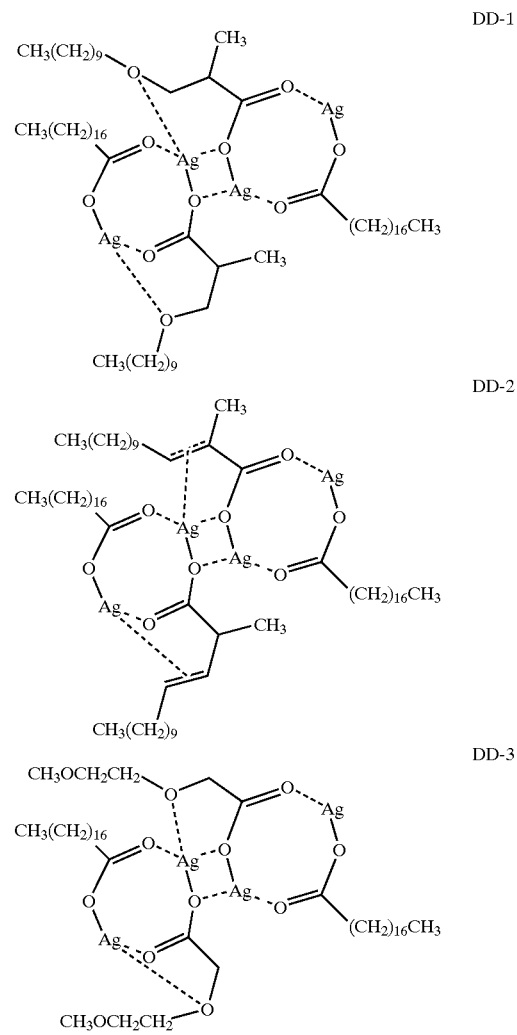

In addition, the silver dimer compound can have a core-shell construction as described above, and further wherein the at least one of the silver carboxylates used in the core and/or shell is substituted in the α- or β-position with the silver coordinate covalent bond forming ligand.

Compositions of this invention can include one or more silver dimer compounds of this invention in combination with one more conventional silver salts as described below (that is conventional silver salts that have one or more molecules of the same silver salt).

The conventional non-photosensitive source of reducible silver ions used in photothermographic materials can be any material that contains reducible silver ions in catalytic association with the photosensitive silver halide. Preferably, it is a silver salt that is comparatively stable to light and forms a silver image when heated to 80° C. or higher in the presence of an exposed photocatalyst (such as silver halide) and a reducing agent.

Silver salts of organic acids, particularly silver salts of long-chain carboxylic acids are preferred. The chains typically contain 10 to 30, and preferably 15 to 28, carbon atoms. Suitable organic silver salts include silver salts of organic compounds having a carboxylic acid group. Examples thereof include a silver salt of an aliphatic carboxylic acid or a silver salt of an aromatic carboxylic acid. Preferred examples of the silver salts of aliphatic carboxylic acids include silver behenate, silver arachidate, silver stearate, silver oleate, silver laurate, silver caprate, silver myristate, silver palmitate, silver maleate, silver fumarate, silver tartarate, silver furoate, silver linoleate, silver butyrate, silver camphorate, and mixtures thereof. Preferred examples of the silver salts of aromatic carboxylic acid and other carboxylic acid group-containing compounds include, but are not limited to, silver benzoates, a silver-substituted benzoate, such as silver 3,5-dihydroxy-benzoate, silver o-methylbenzoate, silver m-methylbenzoate, silver p-methylbenzoate, silver 2,4-dichlorobenzoate, silver acetamidobenzoate, silver p-phenylbenzoate, silver gallate, silver tannate, silver phthalate, silver terephthalate, silver salicylate, silver phenylacetate, silver pyromellitate, a silver salt of 3-carboxymethyl-4-methyl-4-thiazoline-2-thione or others as described in U.S. Pat. No. 3,785,830 (Sullivan et al.), and silver salts of aliphatic carboxylic acids containing a thioether group as described in U.S. Pat. No. 3,330,663 (Weyde et al.). Soluble silver carboxylates comprising hydrocarbon chains incorporating ether or thioether linkages, or sterically hindered substitution in the α-(on a hydrocarbon group) or ortho-(on an aromatic group) position, and displaying increased solubility in coating solvents and affording coatings with less light scattering can also be used. Such silver carboxylates are described in U.S. Pat. No. 5,491,059 (noted above). Mixtures of any of the silver salts described herein can also be used if desired.

Silver salts of sulfonates are also useful in the practice of this invention. Such materials are described for example in U.S. Pat. No. 4,504,575 (Lee). Silver salts of sulfosuccinates are also useful as described for example in EP-A-0 227 141 (Leenders et al.).

Silver salts of compounds containing mercapto or thione groups and derivatives thereof can also be used. Preferred examples of these compounds include, but are not limited to, a silver salt of 3-mercapto-4-phenyl-1,2,4-triazole, a silver salt of 2-mercaptobenzimidazole, a silver salt of 2-mercapto-5-aminothiadiazole, a silver salt of 2-(2-ethylglycolamido)benzothiazole, silver salts of thioglycolic acids (such as a silver salt of a S-alkylthioglycolic acid, wherein the alkyl group has from 12 to 22 carbon atoms), silver salts of dithiocarboxylic acids (such as a silver salt of dithioacetic acid), a silver salt of thioamide, a silver salt of 5-carboxylic-l-methyl-2-phenyl-4-thiopyridine, a silver salt of mercaptotriazine, a silver salt of 2-mercaptobenzoxazole, silver salts as described in U.S. Pat. No. 4,123,274 (Knight et al.) (for example, a silver salt of a 1,2,4-mercaptothiazole derivative, such as a silver salt of 3-amino-5-benzylthio-1,2,4-thiazole), and silver salts of thione compounds [such as a silver salt of 3-(2-carboxyethyl)-4-methyl-4-thiazoline-2-thione as described in U.S. Pat. No. 3,201,678 (Meixell)].

Furthermore, a silver salt of a compound containing an imino group can be used. Preferred examples of these compounds include, but are not limited to, silver salts of benzotriazole and substituted derivatives thereof (for example, silver methylbenzotriazole and silver 5-chlorobenzotriazole), silver salts of 1,2,4-triazoles or 1-H-tetrazoles such as phenylmercaptotetrazole as described in U.S. Pat. No. 4,220,709 (deMauriac), and silver salts of imidazoles and imidazole derivatives as described in U.S. Pat. No. 4,260,677 (Winslow et al.). Moreover, silver salts of acetylenes can also be used as described, for example in U.S. Pat. No. 4,761,361 (Ozaki et al.) and U.S. Pat. No. 4,775,613 (Hirai et al.).

It is also convenient to use silver half soaps. A preferred example of a silver half soap is an equimolar blend of silver carboxylate and carboxylic acid, which analyzes for about 14.5% by weight solids of silver in the blend and which is prepared by precipitation from an aqueous solution of the sodium salt of a commercial fatty carboxylic acid, or by addition of the free fatty acid to the silver soap. For transparent films a silver carboxylate full soap, containing not more than about 15% of free carboxylic acid and analyzing for about 22% silver, can be used. For opaque photothermographic materials, different amounts can be used.

The methods used for making silver soap emulsions are well known in the art and are disclosed in *Research Disclosure,* April 1983, item 22812, *Research Disclosure,* October 1983, item 23419, U.S. Pat. No. 3,985,565 (Gabrielsen et al.), and the references cited above.

The photocatalyst and the non-photosensitive source of reducible silver ions must be in catalytic proximity (that is, reactive association). "Catalytic proximity" or "reactive association" means that they should be in the same layer, or in adjacent layers. It is preferred that these reactive components be present in the same emulsion layer.

The one or more non-photosensitive sources of reducible silver ions (including the silver dimer compounds of this invention) are preferably present in an amount of about 5% by weight to about 70% by weight, and more preferably, about 10% to about 50% by weight, based on the total dry weight of the emulsion layers. Stated another way, the amount of the sources of reducible silver ions is generally present in an amount of from about 0.001 to about 0.2 mol/m$^2$ of the dry photothermographic material, and preferably from about 0.01 to about 0.05 mol/m$^2$ of that material.

The total amount of silver (from all silver sources) in the photothermographic materials is generally at least 0.002 mol/m$^2$ and preferably from about 0.01 to about 0.05 mol/m$^2$.

Reducing Agents

For black-and-white imaging materials, the reducing agent (or reducing agent composition comprising two or more components) for the source of reducible silver ions can be any material, preferably an organic material, that can reduce silver (I) ion to metallic silver. Conventional photographic developers such as methyl gallate, hydroquinone, substituted hydroquinones, hindered phenols, amidoximes, azines, catechol, pyrogallol, ascorbic acid (and derivatives thereof), leuco dyes and other materials readily apparent to one skilled in the art can be used in this manner as described for example in U.S. Pat. No. 6,020,117 (Bauer et al.).

In some instances, the reducing agent composition comprises two or more components such as a hindered phenol developer and a co-developer that can be chosen from the various classes of reducing agents described below. Ternary developer mixtures involving the further addition of contrast enhancing agents are also useful. Such contrast enhancing agents can be chosen from the various classes of reducing agents described below.

Hindered phenol reducing agents are preferred (alone or in combination with one or more co-developers and contrast enhancing agents). These are compounds that contain only one hydroxy group on a given phenyl ring and have at least one additional substituent located ortho to the hydroxy group. Hindered phenol developers may contain more than one hydroxy group as long as each hydroxy group is located on different phenyl rings. Hindered phenol developers include, for example, binaphthols (that is dihydroxybinaphthyls), biphenols (that is dihydroxybiphenyls), bis(hydroxynaphthyl)methanes, bis (hydroxyphenyl)methanes, hindered phenols, and hindered naphthols each of which may be variously substituted.

Representative binaphthols include, but are not limited, to 1,1'-bi-2-naphthol, 1,1'-bi-4-methyl-2-naphthol and 6,6'-dibromo-bi-2-naphthol. For additional compounds see U.S. Pat. No. 3,094,417 (Workman) and U.S. Pat. No. 5,262,295 (Tanaka et al.), both incorporated herein by reference.

Representative biphenols include, but are not limited, to 2,2'-dihydroxy-3,3'-di-t-butyl-5,5-dimethylbiphenyl, 2,2'-dihydroxy-3,3',5,5'-tetra-t-butylbiphenyl, 2,2'-dihydroxy-3,3'-di-t-butyl-5,5'-dichloro-biphenyl, 2-(2-hydroxy-3-t-butyl-5-methylphenyl)-4-methyl-6-n-hexylphenol, 4,4'-dihydroxy-3,3',5,5'-tetra-t-butylbiphenyl and 4,4'-dihydroxy-3,3',5,5'-tetramethylbiphenyl. For additional compounds see U.S. Pat. No. 5,262,295 (noted above).

Representative bis(hydroxynaphthyl)methanes include, but are not limited to, 4,4'-methylenebis(2-methyl-1-naphthol). For additional compounds see U.S. Pat. No. 5,262,295 (noted above).

Representative bis(hydroxyphenyl)methanes include, but are not limited to, bis(2-hydroxy-3-t-butyl-5-methylphenyl)methane (CAO-5), 1,1-bis(2-hydroxy-3,5-dimethylphenyl)-3,5,5-trimethylhexane (NONOX or PERMANAX WSO), 1,1-bis(3,5-di-t-butyl-4-hydroxyphenyl)methane, 2,2-bis(4-hydroxy-3-methylphenyl)propane, 4,4-ethylidene-bis(2-t-butyl-6-methylphenol), 2,2'-isobutylidene-bis(4,6-dimethylphenol) (LOWINOX 221B46), and 2,2-bis(3,5-dimethyl-4-hydroxyphenyl)propane. For additional compounds see U.S. Pat. No. 5,262,295 (noted above).

Representative hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol and 2-t-butyl-6-methylphenol.

Representative hindered naphthols include, but are not limited to, 1-naphthol, 4-methyl-1-naphthol, 4-methoxy-1-naphthol, 4-chloro-1-naphthol and 2-methyl-1-naphthol. For additional compounds see U.S. Pat. No. 5,262,295 (noted above).

More specific alternative reducing agents that have been disclosed in dry silver systems including amidoximes such as phenylamidoxime, 2-thienyl-amidoxime and p-phenoxyphenylamidoxime, azines (for example, 4-hydroxy-3,5-dimethoxybenzaldehydrazine), a combination of aliphatic carboxylic acid aryl hydrazides and ascorbic acid, such as 2,2'-bis(hydroxymethyl)-propionyl-β-phenyl hydrazide in combination with ascorbic acid, a combination of polyhydroxybenzene and hydroxylamine, a reductone and/or a hydrazine [for example, a combination of hydroquinone and bis(ethoxyethyl)hydroxylamine], piperidinohexose reductone or formyl-4-methylphenylhydrazine, hydroxamic acids (such as phenylhydroxamic acid, p-hydroxyphenylhydroxamic acid, and o-alanine-hydroxamic acid), a combination of azines and sulfonamidophenols (for example, phenothiazine and 2,6-dichloro-4-benzenesulfonamidophenol), α-cyanophenylacetic acid derivatives (such as ethyl α-cyano-2-methylphenylacetate and ethyl α-cyanophenylacetate), bis-o-naphthols [such as 2,2'-dihydroxyl-1-binaphthyl, 6,6'-dibromo-2,2'-dihydroxy-1,1'-binaphthyl, and bis(2-hydroxy-1-naphthyl)-methane], a combination of bis-o-naphthol and a 1,3-dihydroxybenzene derivative (for example, 2,4-dihydroxybenzophenone or 2,4-dihydroxyacetophenone), 5-pyrazolones such as 3-methyl-1-phenyl-5-pyrazolone, reductones (such as dimethylaminohexose reductone, anhydrodihydro-aminohexose reductone and anhydrodihydro-piperidone-hexose reductone), sulfonamidophenol reducing agents (such as 2,6-dichloro-4-benzenesulfonamido-phenol, and p-benzenesulfon-amidophenol), 2-phenylindane-1,3-dione and similar compounds, chromans (such as 2,2-dimethyl-7-t-butyl-6-hydroxychroman), 1,4-dihydropyridines (such as 2,6-dimethoxy-3,5-dicarbethoxy-1 4-dihydropyridine), bisphenols [such as bis(2-hydroxy-3-t-butyl-5-methylphenyl)methane, 2,2-bis(4-hydroxy-3-methylphenyl) propane, 4,4-ethylidene-bis(2-t-butyl-6-methylphenol) and 2,2-bis(3,5-dimethyl-4-hydroxyphenyl)propane], ascorbic acid derivatives (such as 1-ascorbylpalmitate, ascorbylstearate and unsaturated aldehydes and ketones), 3-pyrazolidones, and certain indane-1,3-diones.

An additional class of reducing agents that can be used as developers are substituted hydrazines including the sulfonyl hydrazides described in U.S. Pat. No. 5,464,738 (Lynch et al.). Still other useful reducing agents are described, for example, in U.S. Pat. No. 3,074,809 (Owen), U.S. Pat. No. 3,094,417 (Workman), U.S. Pat. No. 3,080,254 (Grant, Jr.) and U.S. Pat. No. 3,887,417 (Klein et al.). Auxiliary reducing agents may be useful as described in U.S. Pat. No. 5,981,151 (Leenders et al.).

Useful co-developer reducing agents can also be used as described for example, in copending U.S. Ser. No. 09/239, 182 (filed Jan. 28, 1999 by Lynch and Skoog), incorporated herein by reference. Examples of these compounds include, but are not limited to, 2,5-dioxo-cyclopentane carboxaldehyde, 5-(hydroxymethylene)-2,2-dimethyl-1,3-dioxane-4,6-dione, 5-(hydroxymethylene)-1,3-dialkylbarbituric acids, 2-(ethoxymethylene)-1H-indene-1,3 (2H)-dione.

Additional classes of reducing agents that can be used as co-developers are trityl hydrazides and formyl phenyl hydrazides as described in U.S. Pat. No. 5,496,695 (Simpson et al.), 2-substituted malondialdehyde compounds as described in U.S. Pat. No. 5,654,130 (Murray), and 4-substituted isoxazole compounds as described in U.S. Pat. No. 5,705,324 (Murray). Still other useful co-developers include 2,5-dioxo-cyclopentane carboxaldehydes, 5-(hydroxymethylene)-1,3-dialkylbarbituric acids, and 2-(ethoxymethylene)-1H-indene-1,3(2H)-diones. Additional developers are described in U.S. Pat. No. 6,100,022 (Inoue et al.). All of the patents above are incorporated herein by reference.

Yet another class of co-developers are substituted acrylonitrile compounds that can be represented by structure III as follows:

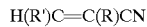　　　　　　　　　　　　　　　　III wherein R is a substituted or unsubstituted aryl group of 6 to 14 carbon atoms in the single or fused ring structure (such as phenyl, naphthyl, p-methylphenyl, p-chlorophenyl, 4-pyridinyl and o-nitrophenyl groups) or an electron withdrawing group (such as a halo atom, cyano group, carboxy group, ester group and phenylsulfonyl group). R' is a halo group (such as fluoro, chloro and bromo), hydroxy or metal salt thereof, a thiohydrocarbyl group, an oxyhydroxycarbyl group, or a substituted or unsubstituted 5- or 6-membered aromatic heterocyclic group having only carbon atoms and 1 to 4 nitrogen atoms in the central ring (with or without fused rings attached), and being attached through a nonquaternary ring nitrogen atom (such as pyridyl, furyl, diazolyl, triazolyl, pyrrolyl, tetrazolyl, benzotriazolyl, benzopyrrolyl and quinolinyl groups). Further details of these compounds and their preparation can be found in U.S. Pat. No. 5,635,339 (Murray) and U.S. Pat. No. 5,545,515 (Murray et al.), both incorporated herein by reference.

Examples of such compounds include, but are not limited to, the compounds identified as HET-01 and HET-02 in U.S. Pat. No. 5,635,339 (noted above) and CN-01 through CN-13 in U.S. Pat. No. 5,654,130 (noted above). Particularly useful compounds of this type are (hydroxymethylene) cyanoacetates and their metal salts.

Various contrast enhancers can be used in some photothermographic materials with specific co-developers. Examples of useful contrast enhancers include, but are not limited to, hydroxylamines (including hydroxylamine and alkyl- and aryl-substituted derivatives thereof), alkanolamines and ammonium phthalamate compounds as described for example, in U.S. Pat. No. 5,545,505 (Simpson), hydroxamic acid compounds as described for example, in U.S. Pat. No. 5,545,507 (Simpson et al.), N-acylhydrazine compounds as described for example, in U.S. Pat. No. 5,558,983 (Simpson et al.), and hydrogen atom donor compounds as described in U.S. Pat. No. 5,637,449 (Harring et al.). All of the above patents are incorporated herein by reference.

The reducing agent (or mixture thereof) described herein is generally present as 1 to 10% (dry weight) of the emulsion layer. In multilayer constructions, if the reducing agent is added to a layer other than an emulsion layer, slightly higher proportions, of from about 2 to 15 weight % may be more desirable. Any co-developers may be present generally in an amount of from about 0.001% to about 1.5% (dry weight) of the emulsion layer coating.

For color imaging materials (for example, monochrome, dichrome, or full color images), one or more reducing agents can be used that can be oxidized directly or indirectly to form or release one or more dyes. The dye-forming or -releasing compound may be any colorless or lightly colored compound that can be oxidized to a colored form, when heated, preferably to a temperature of from about 80° C. to about 250° C. for a duration of at least 1 second. When used with a dye- or image-receiving layer, the dye can diffuse through the imaging layers and interlayers into the image-receiving layer of the thermographic or photothermographic material.

Leuco dyes or "blocked" leuco dyes are one class of dye-releasing compounds (or "blocked" dye-releasing compounds) that form or release a dye upon oxidation by silver ion to form a visible color image in the practice of the present invention. Leuco dyes are the reduced form of dyes that are generally colorless or very lightly colored in the visible region (optical density of less than 0.2). Thus, oxidation provides a color change, that is from colorless to colored, or an optical density increase of at least 0.2 units, or a substantial change in hue.

Representative classes of useful leuco dyes include, but are not limited to, chromogenic leuco dyes (such as indoaniline, indophenol, or azomethine dyes), imidazole leuco dyes such as 2-(3,5-di-t-butyl-4-hydroxyphenyl)-4,5-diphenylimidazole as described for example in U.S. Pat. No. 3,985,565 (Gabrielson et al.), dyes having an azine, diazine, oxazine, or thiazine nucleus such as those described for example in U.S. Pat. No. 4,563,415 (Brown et al.), U.S. Pat. No. 4,622,395 (Bellus et al.), U.S. Pat. No. 4,710,570 (Thien), and U.S. Pat. No. 4,782,010 (Mader et al.), and benzlidene leuco compounds as described for example in U.S. Pat. No. 4,932,792 (Grieve et al.). All of the references cited in the preceeding sentence are incorporated herein by reference. Further details about the chromogenic leuco dyes noted above can be obtained from U.S. Pat. No. 5,491,059 (noted above, Column 13) and references noted therein.

Another useful class of leuco dyes are what are known as "aldazine" and "ketazine" leuco dyes, which are described for example in U.S. Pat. No. 4,587,211 (Ishida et al.) and U.S. Pat. No. 4,795,697 (Vogel et al.), both incorporated herein by reference.

Still another useful class of dye-releasing compounds that form diffusible dyes upon oxidation are known as preformed dye release (PDR) or redox dye release (RDR) compounds. In such compounds, the reducing agents for the nonphotosensitive silver dimer compound of this invention release a mobile preformed dye upon oxidation. Examples of such compounds are described in U.S. Pat. No. 4,981,775 (Swain), incorporated herein by reference.

Further, other useful image-forming compounds are those in which the mobility of a dye moiety changes as a result of an oxidation-reduction reaction with silver halide, or a nonphotosensitive silver salt (such as the silver dimer compounds of this invention), at high temperature, as described for example in JP Patent Application 165,054/84.

Still further the reducing agent can be a compound that releases a conventional photographic dye forming color coupler or developer upon oxidation as is known in the photographic art.

The dyes that are formed or released can be the same in the same or different imaging layers. A difference of at least 60 nm in reflective maximum absorbance is preferred. More preferably, this difference is from about 80 to about 100 nm. Further details about the various dye absorbances are provided in U.S. Pat. No. 5,491,059 (noted above, Col. 14).

The total amount of one or more leuco dyes that can be incorporated into the thermographic or photothermographic materials of this invention is generally from about 0.5 to about 25 weight % of the total dye weight of each imaging layer in which they are located. Preferably, the amount in each imaging layer is from about 1 to about 10 weight %, based on the total dry layer weight. The useful relative proportions of the leuco dyes would be readily known to a skilled worker in the art.

Other Addenda

The thermographic and photothermographic materials of the invention can also contain other additives such as shelf-life stabilizers, toners, antifoggants, contrast enhancers, development accelerators, acutance dyes, post-processing stabilizers or stabilizer precursors, and other image-modifying agents as would be readily apparent to one skilled in the art.

The photothermographic materials of the present invention can be further protected against the production of fog and can be stabilized against loss of sensitivity during storage. While not necessary for the practice of the invention, it may be advantageous to add mercury (II) salts to the emulsion layer(s) as an antifoggant. Preferred mercury (II) salts for this purpose are mercuric acetate and mercuric bromide. Other useful mercury salts include those described in U.S. Pat. No. 2,728,663 (Allen).

Other suitable antifoggants and stabilizers that can be used alone or in combination include thiazolium salts as described in U.S. Pat. No. 2,131,038 (Staud) and U.S. Pat. No. 2,694,716 (Allen), azaindenes as described in U.S. Pat. No. 2,886,437 (Piper), triazaindolizines as described in U.S. Pat. No. 2,444,605 (Heimbach), the urazoles described in U.S. Pat. No. 3,287,135 (Anderson), sulfocatechols as described in U.S. Pat. No. 3,235,652 (Kennard), the oximes described in GB 623,448 (Carrol et al.), polyvalent metal salts as described in U.S. Pat. No. 2,839,405 (Jones), thiuronium salts as described in U.S. Pat. No. 3,220,839 (Herz), palladium, platinum and gold salts as described in U.S. Pat. No. 2,566,263 (Trirelli) and U.S. Pat. No. 2,597,915 (Damshroder), and 2-(tribromomethyl-sulfonyl) quinoline compounds as described in U.S. Pat. No. 5,460,938 (Kirk et al.). Stabilizer precursor compounds capable of releasing stabilizers upon application of heat during development can also be used. Such precursor compounds are described in for example, U.S. Pat. No. 5,158,866 (Simpson et al.), U.S. Pat. No. 5,175,081 (Krepski et al.), U.S. Pat. No. 5,298,390 (Sakizadeh et al.), and U.S. Pat. No. 5,300,420 (Kenney et al.).

In addition, certain substituted-sulfonyl derivatives of benzotriazoles (for example alkylsulfonylbenzotriazoles and arylsulfonylbenzo-triazoles) have been found to be useful stabilizing compounds (such as for post-processing print stabilizing), as described in U.S. Pat. No. 6,171,767B1 (Kong et al).

Furthermore, other specific useful antifoggants/stabilizers are described in more detail in U.S. Pat. No. 6,083,681 (Lynch et al.), incorporated herein by reference.

Other antifoggants are hydrobromic acid salts of heterocyclic compounds (such as pyridinium hydrobromide perbromide) as described, for example, in U.S. Pat. No. 5,028,523 (Skoug), compounds having —$SO_2CBr_3$ groups as described for example in U.S. Pat. No. 5,594,143 (Kirk et al.) and U.S. Pat. No. 5,374,514 (Kirk et al.), benzoyl acid compounds as described, for example, in U.S. Pat. No. 4,784,939 (Pham), substituted propenenitrile compounds as described, for example, in U.S. Pat. No. 5,686,228 (Murray et al.), silyl blocked compounds as described, for example, in U.S. Pat. No. 5,358,843 (Sakizadeh et al.), vinyl sulfones as described, for example, in EP-A-0 600,589 (Philip, Jr. et al.) and EP-A-0 600,586 (Philip, Jr. et al.), and tribromomethylketones as described, for example, in EP-A-0 600,587 (Oliff et al.).

Preferably, the photothermographic materials of this invention include one or more polyhalo antifoggants that include one or more polyhalo substituents including but not limited to, dichloro, dibromo, trichloro, and tribromo groups. The antifoggants can be aliphatic, alicyclic or aromatic compounds, including aromatic heterocyclic and carbocyclic compounds.

The use of "toners" or derivatives thereof that improve the image is highly desirable. Preferably, if used, a toner can be present in an amount of about 0.01% by weight to about 10%, and more preferably about 0.1% by weight to about 10% by weight, based on the total dry weight of the layer in which it is included. Toners may be incorporated in the thermographic and photothermo-graphic emulsion layer or in an adjacent layer. Toners are well known materials in the thermographic and photothermographic art, as shown in U.S. Pat. No. 3,080,254 (Grant, Jr.), U.S. Pat. No. 3,847,612 (Winslow), U.S. Pat. No. 4,123,282 (Winslow), U.S. Pat. No. 4,082,901 (Laridon et al.), U.S. Pat. No. 3,074,809 (Owen), U.S. Pat. No. 3,446,648 (Workman), U.S. Pat. No. 3,844,797 (Willems et al.), U.S. Pat. No. 3,951,660 (Hagemann et al.), U.S. Pat. No. 5,599,647 (Defieuw et al.) and GB 1,439,478 (Agfa-Gevaert).

Examples of toners include, but are not limited to, phthalimide and N-hydroxyphthalimide, cyclic imides (such as succinimide), pyrazoline-5-ones, quinazolinone, 1-phenylurazole, 3-phenyl-2-pyrazoline-5-one, and 2,4-thiazolidinedione, naphthalimides (such as N-hydroxy-1,8-naphthalimide), cobalt complexes [such as hexaaminecobalt (3+) trifluoroacetate], mercaptans (such as 3-mercapto-1,2,4-triazole, 2,4-dimercaptopyrimidine, 3-mercapto-4,5-diphenyl-1,2,4-triazole and 2,5-dimercapto-1,3,4-thiadiazole), N-(amino-methyl)aryldicarboximides (such as (N,N-dimethylaminomethyl)phthalimide, and N-(dimethylaminomethyl)naphthalene-2,3-dicarboximide, a combination of blocked pyrazoles, isothiuronium derivatives, and certain photobleach agents [such as a combination of N,N'-hexamethylene-bis(1-carbamoyl-3,5-dimethyl-pyrazole), 1,8-(3,6-diazaoctane)bis (isothiuronium)trifluoroacetate, and 2-(tribromomethylsulfonyl benzothiazole)], merocyanine dyes {such as 3-ethyl-5-[(3-ethyl-2-benzothiazolinylidene)-1-methyl-ethylidene]-2-thio-2,4-o-azolidine-dione}, phthalazine and derivatives thereof [such as those described in U.S. Pat. No. 6,146,822 (Asanuma et al.)], phthalazinone and phthalazinone derivatives, or metal salts or these derivatives [such as 4-(1-naphthyl)phthalazinone, 6-chlorophthalazinone, 5,7-dimethoxyphthalazinone, and 2,3-dihydro-1,4-phthalazinedione], a combination of phthalazine (or derivative thereof) plus one or more phthalic acid derivatives (such as phthalic acid, 4-methylphthalic acid, 4-nitrophthalic acid, and tetrachlorophthalic anhydride), quinazolinediones, benzoxazine or naphthoxazine derivatives, rhodium complexes functioning not only as tone modifiers but also as sources of halide ion for silver halide formation in situ [such as ammonium hexachlororhodate (III), rhodium bromide, rhodium nitrate, and potassium hexachlororhodate (III)], inorganic peroxides and persulfates (such as ammonium peroxydisulfate and hydrogen peroxide), benzoxazine-2,4-diones (such as 1,3-benzoxazine-2,4-dione, 8-methyl-1,3-benzoxazine-2,4-dione and 6-nitro-1,3-benzoxazine-2,4-dione), pyrimidines and asym-triazines (such as 2,4-dihydroxypyrimidine, 2-hydroxy-4-amino-pyrimidine and azauracil) and tetraazapentalene derivatives [such as 3,6-dimercapto-1,4-diphenyl-1H,4H-2,3a,5,6a-tetraazapentalene and 1,4-di-(o-chlorophenyl)-3,6-dimercapto-1H,4H-2,3a,5,6a-tetraazapentalene].

Phthalazines and phthalazine derivatives [such as those described in U.S. Pat. No. 6,146,822 (noted above), incorporated herein by reference] are particularly useful toners.

Binders

The photocatalyst (such as photosensitive silver halide), when used, the non-photosensitive source of reducible silver ions, the reducing agent composition, and any other additives used in the present invention are generally added to one or more binders that are either hydrophilic or hydrophobic. Thus, either aqueous- or solvent-based formulations can be used to prepare the thermographic and photothermographic materials of this invention. Mixtures of either or both types of binders can also be used. It is preferred that the binder be selected from hydrophobic polymeric materials, such as, for example, natural and synthetic resins that are sufficiently polar to hold the other ingredients in solution or suspension.

Examples of typical hydrophobic binders include, but are not limited to, polyvinyl acetals, polyvinyl chloride, polyvinyl acetate, cellulose acetate, cellulose acetate butyrate, polyolefins, polyesters, polystyrenes, polyacrylonitrile, polycarbonates, methacrylate copolymers, maleic anhydride ester copolymers, butadiene-styrene copolymers, and other materials readily apparent to one skilled in the art. Copolymers (including terpolymers) are also included in the definition of polymers. The polyvinyl acetals (such as polyvinyl butyral and polyvinyl formal) and vinyl copolymers (such as polyvinyl acetate and polyvinyl chloride) are particularly preferred. Particularly suitable binders are polyvinyl butyral resins that are available as BUTVAR® B79 (Solutia, Inc.) and Pioloform BS-18 or Pioloform BL-16 (Wacker Chemical Company).

Examples of useful hydrophilic binders include, but are not limited to, gelatin and gelatin-like derivatives (hardened or unhardened), cellulosic materials such as cellulose acetate, cellulose acetate butyrate, hydroxymethyl cellulose, acrylamide/methacrylamide polymers, acrylic/methacrylic polymers polyvinyl pyrrolidones, polyvinyl acetates, polyvinyl alcohols, and polysaccharides (such as dextrans and starch ethers).

Hardeners for various binders may be present if desired. Useful hardeners are well known and include diisocyanate compounds as described for example in EP-0 600 586B1 and vinyl sulfone compounds as described in EP-0 600 589B1.

Where the proportions and activities of the thermographic and photothermographic materials require a particular developing time and temperature, the binder(s) should be able to withstand those conditions. Generally, it is preferred that the binder not decompose or lose its structural integrity at 120° C. for 60 seconds. It is more preferred that it not decompose or lose its structural integrity at 177° C. for 60 seconds.

The polymer binder(s) is used in an amount sufficient to carry the components dispersed therein. The effective range can be appropriately determined by one skilled in the art. Preferably, a binder is used at a level of about 10% by weight to about 90% by weight, and more preferably at a level of about 20% by weight to about 70% by weight, based on the total dry weight of the layer in which it is included.

Support Materials

The thermographic and photothermographic materials of this invention comprise a polymeric support that is preferably a flexible, transparent film that has any desired thickness and is composed of one or more polymeric materials, depending upon their use. The supports are generally transparent (especially if the material is used as a photomask) or at least translucent, but in some instances, opaque supports may be useful. They are required to exhibit dimensional stability during thermal development and to have suitable adhesive properties with overlying layers. Useful polymeric materials for making such supports include, but are not limited to, polyesters (such as polyethylene terephthalate and polyethylene naphthalate), cellulose acetate and other cellulose esters, polyvinyl acetal, polyolefins (such as polyethylene and polypropylene), polycarbonates, and polystyrenes (and polymers of styrene derivatives). Preferred supports are composed of polymers having good heat stability, such as polyesters and polycarbonates. Polyethylene terephthalate film is the most preferred support. Various support materials are described, for example, in *Research Disclosure,* August 1979, item 18431. A method of making dimensionally stable polyester films is described in *Research Disclosure,* September, 1999, item 42536.

Opaque supports can also be used such as dyed polymeric films and resin-coated papers that are stable to high temperatures.

Support materials can contain various colorants, pigments, antihalation or acutance dyes if desired. Support materials may be treated using conventional procedures (such as corona discharge) to improve adhesion of overlying layers, or subbing or other adhesion-promoting layers can be used. Useful subbing layer formulations include those conventionally used for photographic materials such as vinylidene halide polymers.

Thermographic and Photothermographic Formulations

The formulation for the emulsion layer(s) can be prepared by dissolving and dispersing a hydrophobic binder, the photocatalyst (for photo-thermographic materials), the non-photosensitive source of reducible silver ions, the reducing composition, and optional addenda in an organic solvent, such as toluene, 2-butanone, acetone or tetrahydrofuran.

Alternatively, these components can be formulated with a hydrophilic binder in water or water-organic solvent mixtures to provide aqueous-based coating formulations.

Thermographic and photothermographic materials of this invention can also contain plasticizers and lubricants such as polyalcohols and diols of the type described in U.S. Pat. No. 2,960,404 (Milton et al.), fatty acids or esters such as those described in U.S. Pat. No. 2,588,765 (Robijns) and U.S. Pat. No. 3,121,060 (Duane), and silicone resins such as those described in GB 955,061 (DuPont). The materials can also contain matting agents such as starch, titanium dioxide, zinc oxide, silica, and polymeric beads, including beads of the type described in U.S. Pat. No. 2,992,101 (Jelley et al.) and U.S. Pat. No. 2,701,245 (Lynn). Polymeric fluorinated surfactants may also be useful in one or more layers of the imaging materials for various purposes, such as improving coatability and optical density uniformity as described in U.S. Pat. No. 5,468,603 (Kub).

EP-A-0 792 476 (Geisler et al.) describes various means of modifying the photothermographic materials to reduce what is known as the "woodgrain" effect, or uneven optical density. This effect can be reduced or eliminated by several means, including treatment of the support, adding matting agents to the topcoat, using acutance dyes in certain layers, or other procedures described in the noted publication.

The thermographic and photothermographic materials can include antistatic or conducting layers. Such layers may contain soluble salts (for example, chlorides or nitrates), evaporated metal layers, or ionic polymers such as those described in U.S. Pat. No. 2,861,056 (Minsk) and U.S. Pat. No. 3,206,312 (Sterman et al.), or insoluble inorganic salts such as those described in U.S. Pat. No. 3,428,451 (Trevoy), electroconductive underlayers such as those described in U.S. Pat. No. 5,310,640 (Markin et al.), electronically-conductive metal antimonate particles such as those described in U.S. Pat. No. 5,368,995 (Christian et al.), and electrically-conductive metal-containing particles dispersed in a polymeric binder such as those described in EP-A-0 678 776 (Melpolder et al.). Other antistatic agents are well known in the art.

The thermographic and photothermographic materials can be constructed of one or more layers on a support. Single layer materials should contain the photocatalyst (for photothermographic materials), the non-photo-sensitive source of reducible silver ions, the reducing composition, the binder, as well as optional materials such as toners, acutance dyes, coating aids and other adjuvants.

Two-layer constructions comprising a single imaging layer coating containing all the ingredients and a protective topcoat are generally found in the materials of this invention. However, two-layer constructions containing photocatalyst and non-photosensitive source of reducible silver ions in one imaging layer (usually the layer adjacent to the support) and the reducing composition and other ingredients in the second imaging layer or distributed between both layers are also envisioned.

Layers to promote adhesion of one layer to another are also known, as described for example, in U.S. Pat. No. 5,891,610 (Bauer et al.), U.S. Pat. No. 5,804,365 (Bauer et al.), and U.S. Pat. No. 4,741,992 (Przezdziecki). Adhesion can also be promoted using specific polymeric adhesive materials as described for example, in U.S. Pat. No. 5,928,857 (Geisler et al.).

Thermographic and photothermographic formulations described herein can be coated by various coating procedures including wire wound rod coating, dip coating, air knife coating, curtain coating, slide coating, or extrusion coating using hoppers of the type described in U.S. Pat. No. 2,681,294 (Beguin). Layers can be coated one at a time, or two or more layers can be coated simultaneously by the procedures described in U.S. Pat. No. 2,761,791 (Russell), U.S. Pat. No. 4,001,024 (Dittman et al.), U.S. Pat. No. 4,569,863 (Keopke et al.), U.S. Pat. No. 5,340,613 (Hanzalik et al.), U.S. Pat. No. 5,405,740 (LaBelle), U.S. Pat. No. 5,415,993 (Hanzalik et al.), U.S. Pat. No. 5,525,376 (Leonard), U.S. Pat. No. 5,733,608 (Kessel et al.), U.S. Pat. No. 5,849,363 (Yapel et al.), U.S. Pat. No. 5,843,530 (Jerry et al.), U.S. Pat. No. 5,861,195 (Bhave et al.), and GB 837,095 (Ilford). A typical coating gap for the emulsion layer can be from about 10 to about 750 μm, and the layer can be dried in forced air at a temperature of from about 20° C. to about 100° C. It is preferred that the thickness of the layer be selected to provide maximum image densities greater than about 0.2, and more preferably, from about 0.5 to 5.0 or more, as measured by a MacBeth Color Densitometer Model TD 504.

When the layers are coated simultaneously using various coating techniques, a "carrier" layer formulation comprising a single-phase mixture of the two or more polymers, described above, may be used. Such formulations are described in copending and commonly assigned U.S. Ser. No. 09/510,648 filed Feb. 23, 2000 by Ludemann et al. that is based on Provisional Application No. 60/121,794, filed Feb. 26, 1999.

Mottle and other surface anomalies can be reduced in the materials of this invention by incorporation of a fluorinated polymer as described for example, in U.S. Pat. No. 5,532,121 (Yonkoski et al.) or by using particular drying techniques as described, for example, in U.S. Pat. No. 5,621,983 (Ludemann et al.).

Preferably, two or more layers are applied to a film support using slide coating. The first layer can be coated on top of the second layer while the second layer is still wet. The first and second fluids used to coat these layers can be the same or different organic solvents (or organic solvent mixtures).

While the first and second layers can be coated on one side of the film support, the method can also include forming on the opposing or backside of said polymeric support, one or more additional layers, including an antihalation layer, an antistatic layer, or a layer containing a matting agent (such as silica), or a combination of such layers. It is also contemplated that the thermographic and photothermographic materials of this invention can include emulsion layers on both sides of the support.

To promote image sharpness, photothermographic materials according to the present invention can contain one or more layers containing acutance and/or antihalation dyes. These dyes are chosen to have absorption close to the exposure wavelength and are designed to absorb scattered light. One or more antihalation dyes may be incorporated into one or more antihalation layers according to known techniques, as an antihalation backing layer, as an antihalation underlayer, or as an antihalation overcoat. Additionally, one or more acutance dyes may be incorporated into one or more frontside layers such as the photothermographic emulsion layer, primer layer, underlayer, or topcoat layer according to known techniques. It is preferred that the photothermographic materials of this invention contain an antihalation coating on the support opposite to the side on which the emulsion and topcoat layers are coated.

Dyes particularly useful as antihalation and acutance dyes include dihydroperimidine squaraine dyes having the nucleus represented by the following general structure:

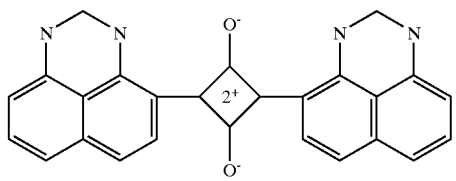

Details of such dyes having the dihydroperimidine squaraine nucleus and methods of their preparation can be found in U.S. Pat. No. 6,063,560 (Suzuki et al.) and U.S. Pat. No. 5,380,635 (Gomez et al.), both incorporated herein by reference. These dyes can also be used as acutance dyes in frontside layers of the materials of this invention. One particularly useful dihydroperimidine squaraine dye is cyclobutenediylium, 1,3-bis[2,3-dihydro-2,2-bis[[1-oxohexyl)oxy]methyl]-1H-perimidin-4-yl]-2,4-dihydroxy-, bis(inner salt).

Dyes particularly useful as antihalation dyes in a backside layer of the photothermographic material also include indolenine cyanine dyes having the nucleus represented by the following general structure:

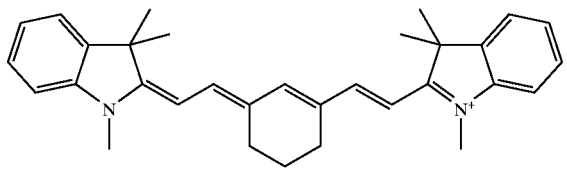

Details of such antihalation dyes having the indolenine cyanine nucleus and methods of their preparation can be found in EP-A-0 342 810 (Leichter), incorporated herein by reference. One particularly useful cyanine dye, compound (6) described therein, is 3H-Indolium, 2-[2-[2-chloro-3-[(1,3-dihydro-1,3,3-trimethyl-2H-indol-2-ylidene)ethylidene]-5-methyl-1-cyclohexen-1-yl]ethenyl]-1,3,3-trimethyl-, perchlorate.

It is also useful in the present invention to employ acutance or antihalation dyes that will decolorize with heat during processing. Dyes and constructions employing these types of dyes are described in, for example, U.S. Pat. No. 5,135,842 (Kitchin et al.), U.S. Pat. No. 5,266,452 (Kitchin et al.), U.S. Pat. No. 5,314,795 (Helland et al.), and EP-A-0 911 693 (Sakurada et al.).

Imaging/Development

While the imaging materials of the present invention can be imaged in any suitable manner consistent with the type of material using any suitable imaging source (typically some type of radiation or electronic signal for photothermographic materials and some type of thermal source for thermographic materials), the following discussion will be directed to the preferred imaging means for photothermographic materials. Generally, the materials are sensitive to radiation in the range of from about 300 to about 850 nm.

Imaging can be achieved by exposing the photothermographic materials to a suitable source of radiation to which they are sensitive, including ultraviolet light, visible light, near infrared radiation and infrared radiation to provide a latent image. Suitable exposure means are well known and include laser diodes that emit radiation in the desired region, photodiodes and others described in the art, including *Research Disclosure*, September 1996, item 38957, (such as sunlight, xenon lamps and fluorescent lamps). Particularly useful exposure means uses laser diodes, including laser diodes that are modulated to increase imaging efficiency using what is known as multilongitudinal exposure techniques as described in U.S. Pat. No. 5,780,207 (Mohapatra et al.). Other exposure techniques are described in U.S. Pat. No. 5,493,327 (McCallum et al.).

For using the materials of this invention, development conditions will vary, depending on the construction used but will typically involve heating the imagewise exposed material at a suitably elevated temperature. Thus, the latent image can be developed by heating the exposed material at a moderately elevated temperature of, for example, from about 50° C. to about 250° C. (preferably from about 80° C. to about 200° C. and more preferably from about 100° C. to about 200° C.) for a sufficient period of time, generally from about 1 to about 120 seconds. Heating can be accomplished using any suitable heating means such as a hot plate, a steam iron, a hot roller or a heating bath.

In some methods, the development is carried out in two steps. Thermal development takes place at a higher temperature for a shorter time (for example, at about 150° C. for up to 10 seconds), followed by thermal diffusion at a lower temperature (for example, at about 80° C.) in the presence of a transfer solvent.

When used in a thermographic element, the image may be developed merely by heating at the above noted temperatures using a thermal stylus or print head, or by heating while in contact with a heat absorbing material.

Thermographic elements of the invention may also include a dye to facilitate direct development by exposure to laser radiation. Preferably the dye is an infrared absorbing dye and the laser is a diode laser emitting in the infrared. Upon exposure to radiation the radiation absorbed by the dye is converted to heat which develops the thermographic element.

Use as a Photomask

The thermographic and photothermographic materials of the present invention are sufficiently transmissive in the range of from about 350 to about 450 nm in non-imaged areas to allow their use in a process where there is a subsequent exposure of an ultraviolet or short wavelength visible radiation sensitive imageable medium. For example, imaging the materials and subsequent development affords a visible image. The heat-developed photothermographic materials absorb ultraviolet or short wavelength visible radiation in the areas where there is a visible image and transmits ultraviolet or short wavelength visible radiation where there is no visible image. The heat-developed materials may then be used as a mask and positioned between a source of imaging radiation (such as an ultraviolet or short wavelength visible radiation energy source) and an imageable material that is sensitive to such imaging radiation, such as a photopolymer, diazo material, photoresist, or photosensitive printing plate. Exposing the imageable material to the imaging radiation through the visible image in the exposed and heat-developed thermographic or photothermographic material provides an image in the imageable material. This process is particularly useful where the imageable medium comprises a printing plate and the thermographic or photothermographic material serves as an image setting film.

The following examples are representative of the present invention and its practice, and are not meant to be limiting in any manner.

EXAMPLE 1

Silver dimer compounds of the present invention were prepared using the following general synthetic method:

Sodium hydroxide (20 mmol) was dissolved in water (150 ml) and heated to 70–75° C. Isopropanol (15 ml) was added followed by $RCO_2H$ (10 mmol) and $R'CO_2H$ (10 mmol) wherein R and R' are defined below. The resulting solution was stirred vigorously 5 minutes and water (15 ml) containing silver nitrate (20 mmol) was added. Water was also added as needed to maintain stirring. The mixture was stirred 10 minutes at 70–75° C. and then placed on a stirrer at room temperature and stirred an additional 30 minutes.

The resulting solid product was filtered, dispersed in an equal volume of water at room temperature, stirred 10 minutes, and filtered again. This procedure was repeated. The solid was broken up and air-dried in the dark. Twenty-four hours later it was dispersed in an equal volume of ether to remove unreacted carboxylic acid, stirred 10 minutes, filtered and air-dried.

The novel silver dimer compounds of this invention were generally characterized by Differential Scanning Calorimetry (DSC) and heating the samples at a rate of 10° C./minute under nitrogen. The compounds so prepared are listed in TABLE II below that also shows the derivatives used for their preparation (generally at a 1:1 molar ratio in the reaction conditions unless otherwise specified). Mass spectra data can be used to confirm the asymmetric structure as was done for some compounds listed below in TABLE II.

TABLE II

| | DSC Peak Temperatures | |
|---|---|---|
| Cpd. | First Transition, ° C. | Second Transition, ° C. |
| D-5 | 100 | 115 |
| D-12 | 123 | 151 |
| D-25 | 95 | 110 |
| D-11 | 120 | 152 |
| D-26 | 97 | 108 |
| D-24 | 126 | 155 |
| D-23 | 96 | 111 |
| D-13 | 129 | — |
| D-27 | 112 | 137 |
| D-28 | 113 | 135 (minor) |
| D-29 | 120 | 139 |
| D-30 | 127 | 154 |

*= negative ion, laser desorption mass spectrum clearly shows the fragmentation pattern for the asymmetric silver dimer: m/z 561 [Ag$(C_{18}H_{35}O_2)(C_{10}H_{19}O_2)$]⁻, 517 [Ag$(C_{17}H_{34})(C_{10}H_{19}O_2)$]⁻.
**= negative ion, laser desorption mass spectrum clearly shows the fragmentation pattern for the asymmetric silver dimer: m/z 467 [Ag$(C_{18}H_{35}O_2)(C_6H_5)$]⁻.

In addition, the preparation of [PHZ($RCO_2$)AgAg($O_2CR'$)PHZ] (analogous to U.S. Pat. No. 5,350,669) was carried out to demonstrate that the novel phthalazine (PHZ) complex of the asymmetric silver dimer compounds could also be prepared and be used as a source of reducible silver ions in a thermographic material.

The resulting novel silver dimer compounds were evaluated as follows:

A thermally-developable imaging emulsion comprising silver dimer $RCO_2AgAgO_2CR'$ (0.4 g) in 5% BUTVAR-72 polyvinyl butyral (10 g) was shaken for 2 hours with glass balls, knife coated 4 mils (0.1 mm) wet, and air-dried. A 2% ethanolic solution of "CAO-5" containing 2% "PHZ" (phthalazine) and 2% "PA" (phthalic acid), when used, was streaked on 1×6 inch (2.5×25 cm) strips and allowed to dry. Thermal Development was carried out by placing the sample on a HOTBENCE™ (Cambridge Instruments, Buffalo, N.Y.) thermal gradient bar for 10 seconds. This provided the temperatures of development onset and maximum density ($T_{onset}$, $T_{Dmax}$). The results, shown in TABLE III below, demonstrate that thermographic materials of the present invention comprising the novel silver dimer compounds can be used for thermographic imaging.

In addition, the coating formulation containing decanoate-Ag—Ag-stearate dimer was remarkably translucent. Thus, the potential for low haze films was demonstrated.

CAO-5 is a developer (reducing agent) and has the structure shown below.

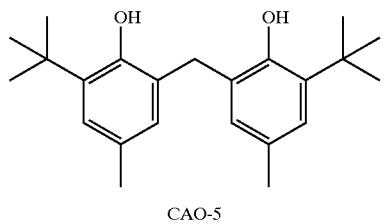

CAO-5

PHZ is phthalazine and has the structure shown below.

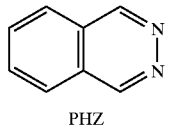

PHZ

PA is phthalic acid and has the structure shown below.

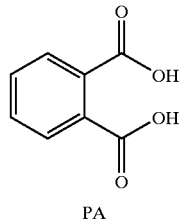

PA

TABLE III

| Cpd. | $T_{onset}$ ° C. | $TD_{max}$ ° C. | Toner |
|---|---|---|---|
| D-29 | 85 | 105 | PHZ |
| D-29 | 80 | 95 | PHZ + PA (grey) |
| D-10 | 88 | 92 | PHZ (black) |
| D-27 | 85 | 98 | PHZ (black) |
| D-28 | 94 | 98 | PHZ (black) |
| D-28 | 100 | 105 | PHZ + PA (grey) |

The silver dimers of this invention can also be used in a color imaging materials. Leuco dyes were used as the color-formers. Development time was 15 seconds. The results are shown in TABLE IV below.

The leuco dyes used in the thermographic elements had the following structures wherein C=cyan, Y=yellow and M=magenta:

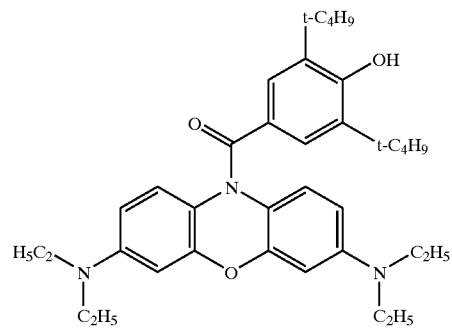

Cyan

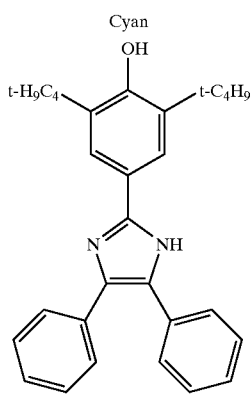

Yellow

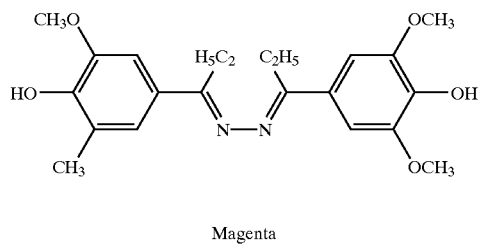

Magenta

TABLE IV

| Cpd. | $T_{onset}$ ° C. | $TD_{max}$ ° C. | Leuco Dye |
|---|---|---|---|
| D-26 | 100 | 125 | M |
|  | 115 | 135 | C |
|  | 120 | 135 | Y |
| D-27 | 130 | >130 | M |
|  | 120 | 135 | C |
|  | 120 | 145 | Y |
| D-28 | 135 | 145 | M |
|  | 95 | 130 | C |
|  | 140 | >145 | Y |
| D-29 | 110 | 130 | M |
|  | 105 | 130 | C |
|  | 125 | 140 | Y |

EXAMPLE 2

The following example demonstrates the use of silver dimer compounds comprising two different silver salts in photothermographic materials.

NaOH (10 mmol) was added to 200 ml of water at 71° C., followed by 5 mmol, each, of two acids (see below). The solution was allowed to cool to just below the Krafft temperature (indicated by the onset of precipitation of the sodium carboxylate) at which point 10 mmol of AgNO$_3$ in 10 ml of H$_2$O were added. The mixture was stirred +minutes, filtered, washed and air dried to provide the desired silver dimer.

The imaging properties of these silver silver dimer compounds were evaluated by homogenizing (10 minutes) a 5% dispersion in polyvinyl butyral, 6% in acetone, with 50 mg CaBr$_2$ in 1 of ethanol. The resultant dispersions were coated at 100 mμ wet thickness on a 4 mil (102 mμ) transparent polyester support. The resulting films were air-dried and coated with a topcoat of 2% PHZ, 2% NONOX, and 2% Pioloform BL-16, applied 50 mμ wet and air dried to provide a photothermographic material.

Samples were evaluated by exposing half (lengthwise) of a strip of the film at 364 nm using a Spectraline ENF-24 ultraviolet lamp followed by thermal development on a HOTBENCH™ thermal gradient bar. In these negative-acting systems, the onset temperatures of the light activated, thermally developed area, $T_{exposed}$, and unexposed, $T_{unexposed}$, demonstrate the imageability of the construction. The results of imaging and heat development of the various invention photothermographic materials are shown below in Table V.

TABLE V

| Cpd | $T_{unexposed}$ | $T_{exposed}$ |
|---|---|---|
| D-1 | 105 | 90 |
| D-2 | 120 | 110 |
| D-7 | 105 | 97 |
| D-3 | 114 | 104 |
| D-4 | 120 | 109 |
| D-28 | 108 | 95 |
| D-6 | 156 | 155 |
| D-17 | 110 | 105 |
| D-8 | 115 | 108 |
| D-9 | 115 | 100 |

EXAMPLE 3

Three thermographic materials were prepared and developed as described in Example 1. Samples CC-1 and CC-2 used symmetrical silver carboxylate dimers. The third sample was prepared using asymmetrical silver dimer compound D-15. The results, shown below in Table VI, demonstrate that the use of asymmetrical silver dimer compounds comprising two different silver salts provides thermographic materials with improved color and higher $D_{max}$.

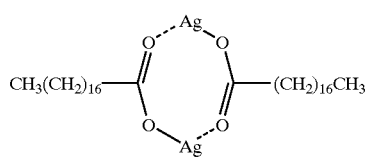
CC-1

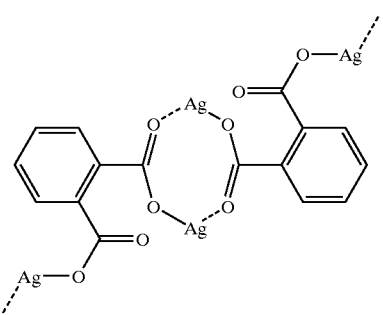
CC-2

TABLE VI

| Cpd. | $T_{onset}$ ° C. | $T D_{max}$ ° C. | Color |
|---|---|---|---|
| CC-1 | 123 | 1.6 | yellow/brown |
| CC-2 | 106 | 1.8 | grey/black |
| D-15 | 105 | 2.6 | black |

The invention has been described in detail with particular reference to certain preferred embodiments thereof, but it will be understood that variations and modifications can be effected within the spirit and scope of the invention.

I claim:

1. A thermally-developable emulsion comprising:
   a) a source of non-photosensitive silver that is a silver dimer compound comprising two different silver salts, provided that when said two different silver salts comprise straight-chain, saturated hydrocarbon groups as silver coordinating ligands, those ligands differ by at least 6 carbon atoms,
   b) a reducing composition for said non-photosensitive silver dimer compound, and
   c) a binder.

2. The thermally-developable emulsion of claim 1 wherein said dimer compound is represented by the following Structure I:

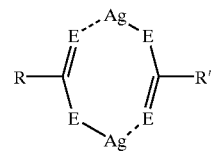

I wherein
   each E is independently oxygen, nitrogen, sulfur, selenium, or tellurium, R and R' are independently alkyl groups, aryl groups, aromatic heterocyclic groups, or halo atoms,
   provided that when E is oxygen, and R and R' are both straight-chain, saturated hydrocarbon groups, then R and R' differ from each other by at least 6 carbon atoms.

3. The thermally developable emulsion of claim 2 wherein E is oxygen, sulfur, or nitrogen, and R and R' are different alkyl groups each having at least 8 carbon atoms.

4. The thermally developable emulsion of claim 3 wherein E is oxygen and R and R' are different alkyl groups each having at least 12 carbon atoms.

5. The thermally developable emulsion of claim 4 wherein R is an alkyl group of 12 to 24 carbon atoms, and R' is an alkyl group of 14 to 24 carbon atoms.

6. The thermally developable emulsion of claim 4 wherein R and R' differ by at least 8 carbon atoms.

7. The thermally developable emulsion of claim 4 wherein either or both of R and R' comprise one or more oxy or thio groups within the alkyl chain.

8. The thermally developable emulsion of claim 2 wherein at least one of R and R' is an aryl group.

9. The thermally developable emulsion of claim 1 wherein at least one of said silver salts comprises a silver aromatic carboxylate.

10. The thermally developable emulsion of claim 1 that is a core-shell compound comprising one or more silver dimer compounds in the core, and one or more different silver dimer compounds in the shell.

11. The thermally developable emulsion of claim 1 comprising one or more of the following compounds D-1 to D-30.

D-1
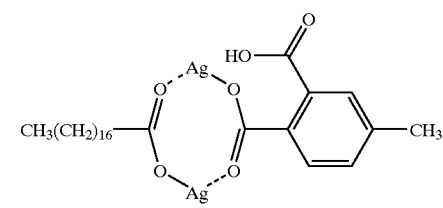

D-2
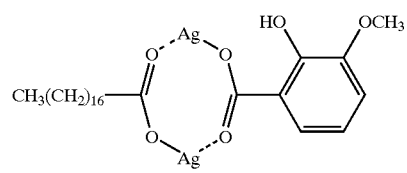

D-3
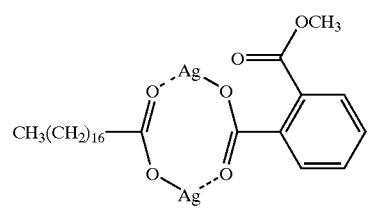

D-4
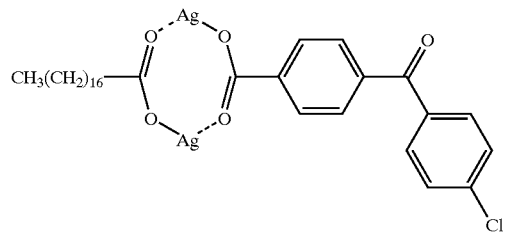

D-5
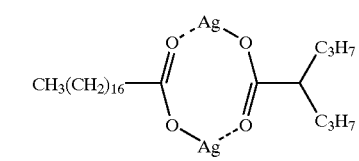

-continued

D-6
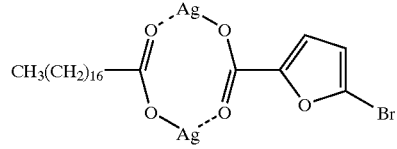

D-7
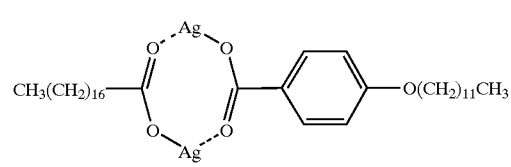

D-8
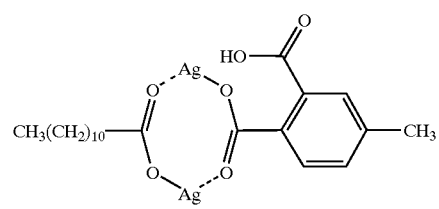

D-9
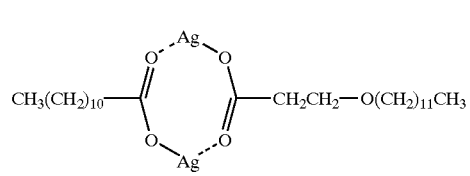

D-10
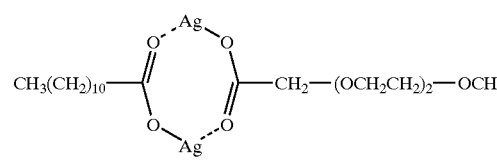

D-11
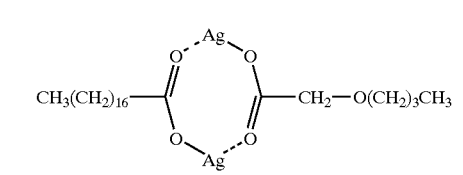

D-12
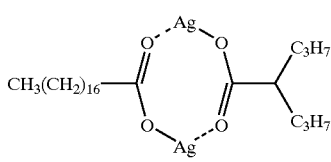

D-13
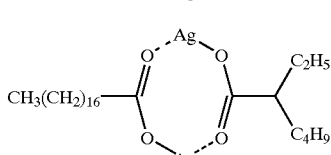

D-14
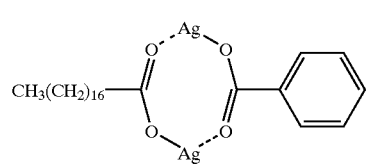

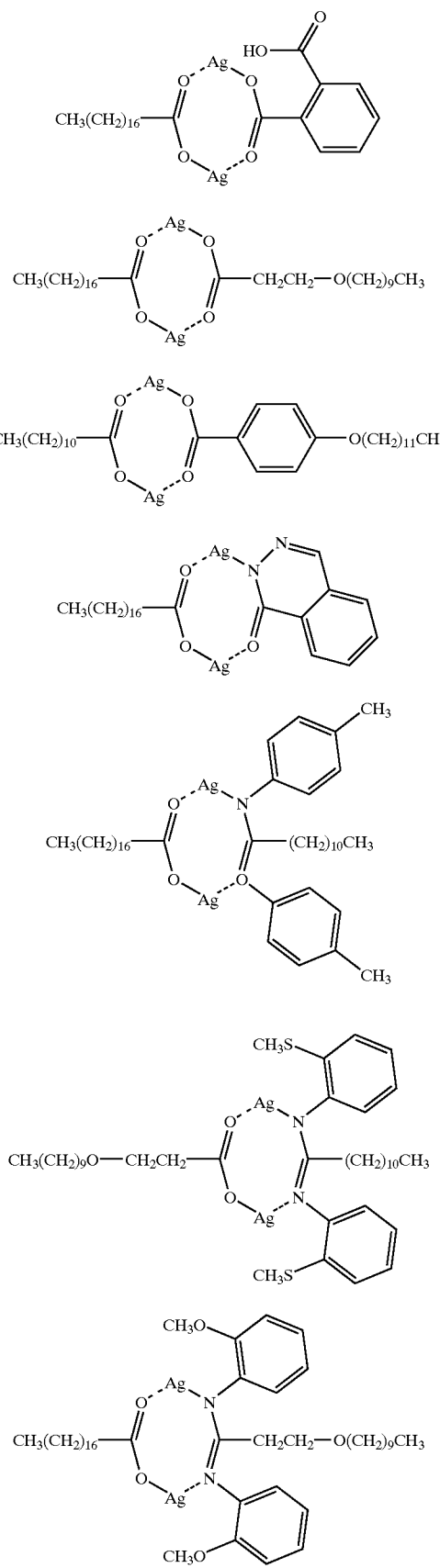
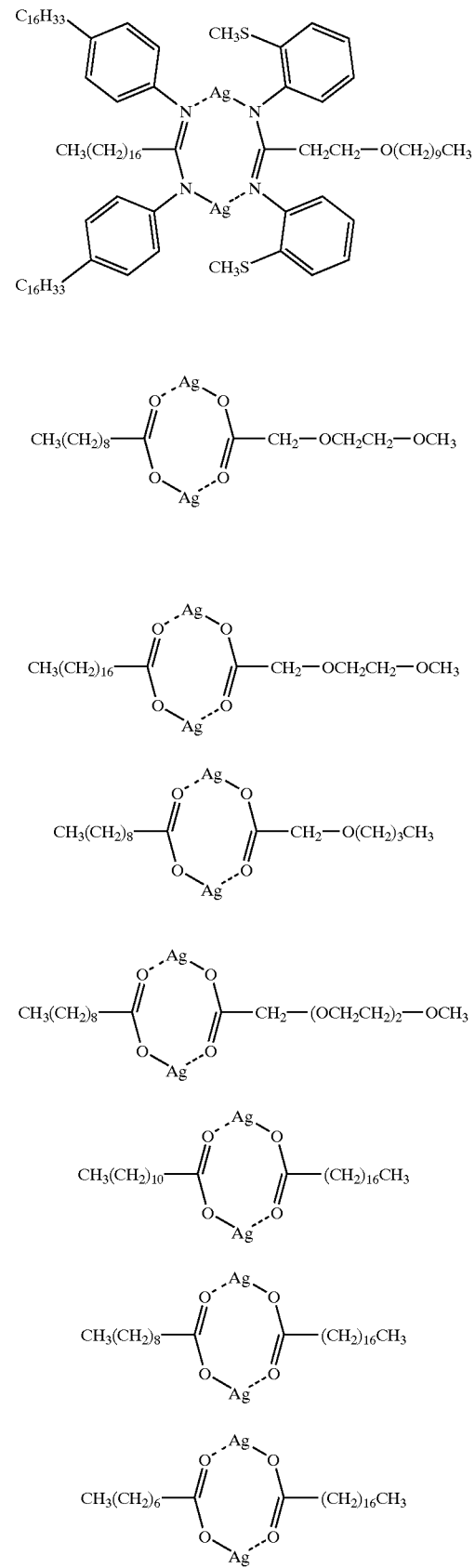

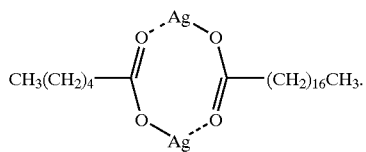
D-30

12. A thermally-developable imaging material comprising a support having thereon, in the same or different thermally-developable imaging layers,
   a) a source of non-photosensitive silver that is a silver dimer compound comprising two different silver salts, provided that when said two different silver salts comprise straight-chain, saturated hydrocarbon groups as silver coordinating ligands, those ligands differ by at least 6 carbon atoms,
   b) a reducing composition for said non-photosensitive silver dimer compound, and
   c) a binder.

13. The thermally-developable imaging material of claim 12 wherein said dimer compound is represented by the following Structure I:

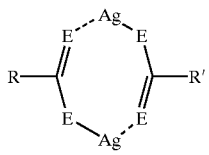
I wherein
   each E is independently oxygen, nitrogen, sulfur, selenium, or tellurium, R and R' are independently alkyl groups, aryl groups, aromatic heterocyclic groups, or halo atoms,
   provided that when E is oxygen, and R and R' are both straight-chain, saturated hydrocarbon groups, then R and R' differ from each other by at least 6 carbon atoms.

14. The thermally developable imaging material of claim 13 wherein E is oxygen, sulfur, or nitrogen, and R and R' are different alkyl groups each having at least 8 carbon atoms.

15. The thermally developable imaging material of claim 14 wherein E is oxygen and R and R' are different alkyl groups each having at least 12 carbon atoms.

16. The thermally developable imaging material of claim 14 wherein R is an alkyl group of 12 to 24 carbon atoms, and R' is an alkyl group of 14 to 24 carbon atoms.

17. The thermally developable imaging material of claim 14 wherein R and R' differ by at least 8 carbon atoms.

18. The thermally developable imaging material of claim 14 wherein either or both of R and R' comprise one or more oxy or thio groups within the alkyl chain.

19. The thermally developable imaging material of claim 13 wherein at least one of R and R' is an aryl group.

20. A method of providing an image comprising imagewise heating the thermally-developable imaging material of claim 12.

21. The thermally developable imaging material of claim 12 wherein at least one of said silver salts comprises a silver aromatic carboxylate.

22. The thermally developable imaging material of claim 12 that is a core-shell compound comprising one or more silver dimer compounds in the core, and one or more different silver dimer compounds in the shell.

23. The thermally developable imaging material of claim 12 comprising one or more of the following compounds D-1 to D-30

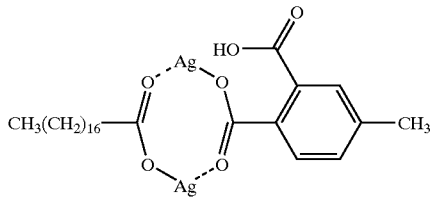
D-1

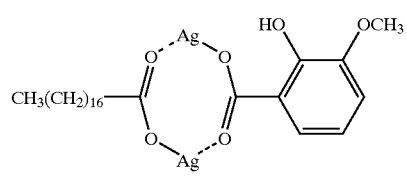
D-2

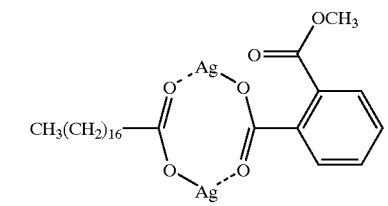
D-3

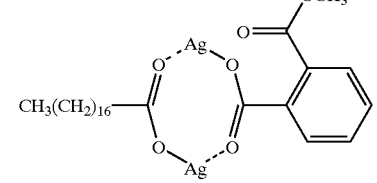
D-4

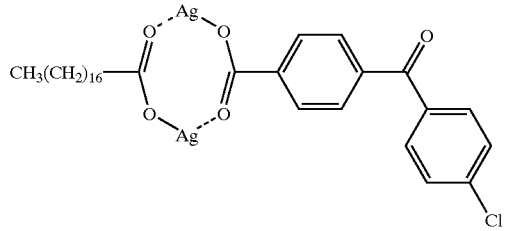
D-5

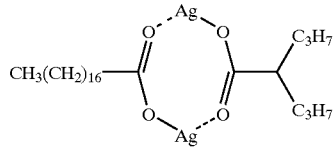
D-6

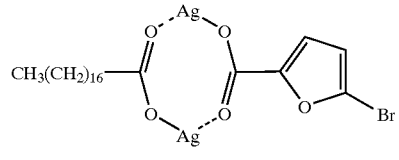
D-7

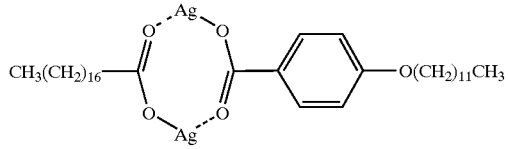

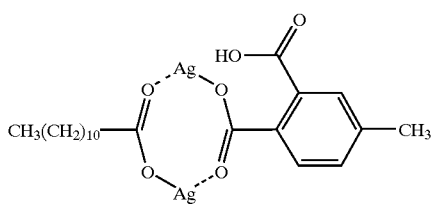
D-8

-continued
D-9
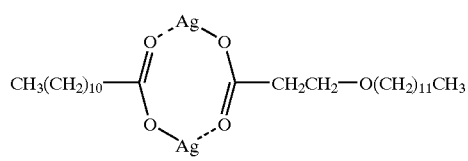
D-10
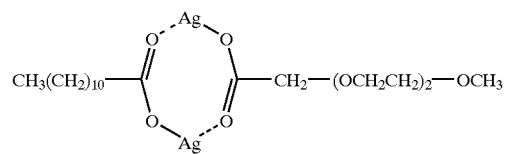
D-11
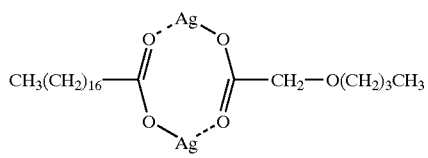
D-12
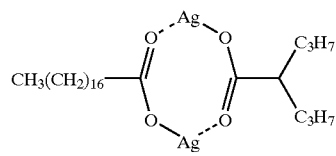
D-13
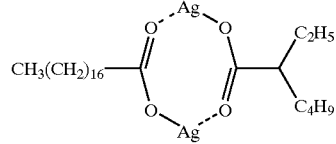
D-14
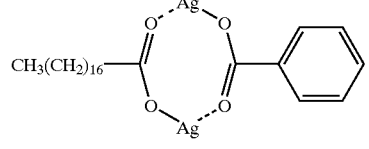
D-15
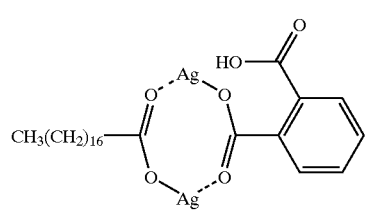
D-16
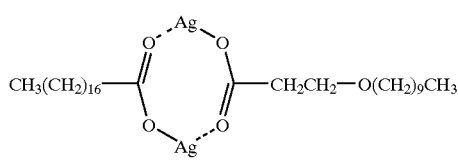
D-17
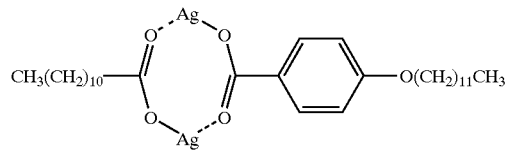
-continued
D-18
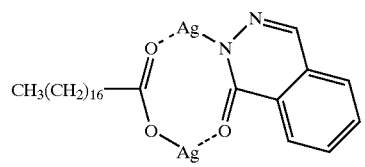
D-19
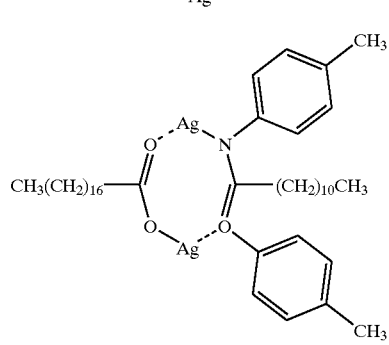
D-20
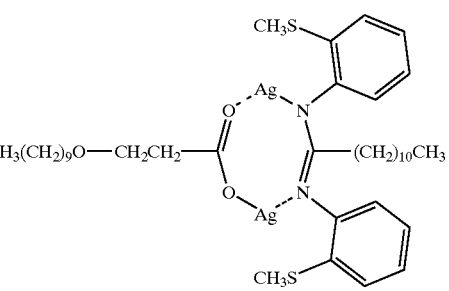
D-21
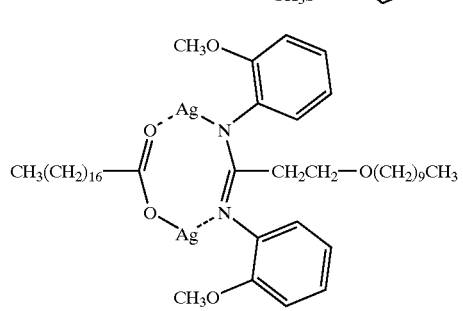
D-22
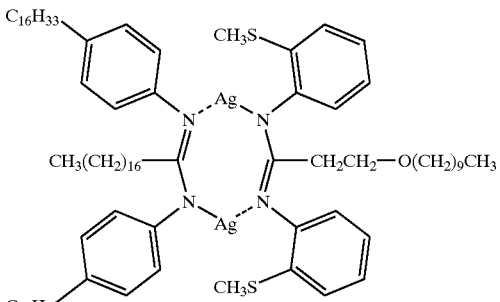
D-23
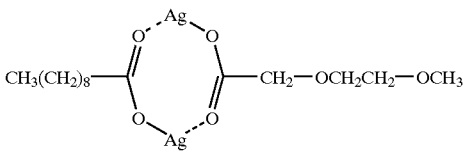

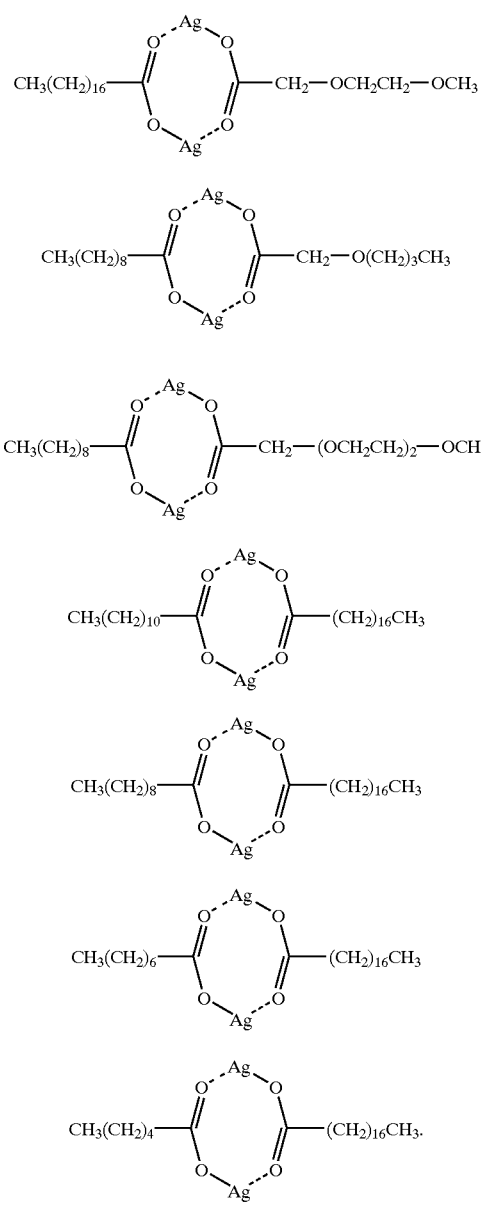

24. A photothermographic material comprising a support having thereon, in one or more photothermographic imaging layers:

a) a photosensitive silver halide, b) a source of non-photosensitive silver that is a silver dimer compound comprising two different silver salts, provided that when said two different silver salts comprise straight-chain, saturated hydrocarbon groups as silver coordinating ligands, those ligands differ by at least 6 carbon atoms, c) a reducing composition for said non-photosensitive silver dimer compound, and d) a binder.

25. The photothermographic material of claim 24 wherein said source of non-photosensitive silver is a silver dimer compound represented by the following Structure I:

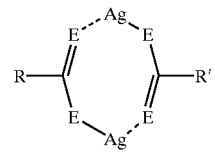

I wherein each E is independently oxygen, nitrogen, sulfur, selenium, or tellurium, R and R' are independently alkyl groups, aryl groups, aromatic heterocyclic groups, or halo atoms, provided that when E is oxygen, and R and R' are both straight-chain, saturated hydrocarbon groups, then R and R' differ from each other by at least 6 carbon atoms.

26. A method of providing an image comprising:

A) imagewise exposing the photothermographic element of claim 24 to imaging radiation to form a latent image, and B) simultaneously or sequentially, heating said exposed photothermo-graphic material to develop said latent image into a visible image.

27. The method of claim 26 wherein said photothermographic material comprises a transparent support, and said method further comprises:

C) positioning said exposed and heat-developed photothermographic material between a source of imaging radiation and an imageable material that is sensitive to said imaging radiation, and D) exposing said imageable material to said imaging radiation through the visible image in said exposed and heat-developed photothermographic material to provide an image in said imageable material.

* * * * *